US012753111B2

(12) United States Patent
Beall et al.

(10) Patent No.: US 12,753,111 B2
(45) Date of Patent: Oct. 6, 2026

(54) ZIRCONIA-TOUGHENED GLASS CERAMICS

(71) Applicant: CORNING INCORPORATED, Corning, NY (US)

(72) Inventors: George Halsey Beall, Big Flats, NY (US); Qiang Fu, Painted Post, NY (US); Charlene Marie Smith, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 19/637,093

(22) Filed: Apr. 2, 2026

(65) Prior Publication Data

US 2026/0225946 A1 Aug. 6, 2026

Related U.S. Application Data

(63) Continuation of application No. 18/383,287, filed on Oct. 24, 2023, which is a continuation of application
(Continued)

(51) Int. Cl.
*C03C 10/00* (2006.01)
*A61K 6/818* (2020.01)
(Continued)

(52) U.S. Cl.
CPC .......... *C03C 10/0027* (2013.01); *A61K 6/818* (2020.01); *A61K 6/822* (2020.01);
(Continued)

(58) Field of Classification Search
CPC . C03C 10/0027; C03C 2214/20; A61K 6/818; A61K 6/833
See application file for complete search history.

(56) References Cited

U.S. PATENT DOCUMENTS 3,804,608 A 4/1974 Gaskell et al.
3,804,609 A 4/1974 Murphy et al.
(Continued)

FOREIGN PATENT DOCUMENTS

CA 2252660 A1 5/1999
CN 101139170 A 3/2008
(Continued)

OTHER PUBLICATIONS

Huang, X., et al. "Microstructure and mechanical properties of zirconia-toughened lithium disilicate glass-ceramic composites." Materials Chemistry and Physics 143.2 (2014): 845-852. (Year: 2014).*

(Continued)

*Primary Examiner* — Cameron K Miller
(74) *Attorney, Agent, or Firm* — Russell S. Magaziner

(57) ABSTRACT

$ZrO_2$-toughened glass-ceramic has high molar fractions of tetragonal $ZrO_2$ and may also include also contain other secondary phases, including lithium silicates, that may be beneficial for toughening or for strengthening through an ion-exchange. Additional secondary phases may also decrease the coefficient of thermal expansion of the glass-ceramic. A method of making such glass-ceramic is also provided.

39 Claims, 12 Drawing Sheets

Related U.S. Application Data

No. 18/096,315, filed on Jan. 12, 2023, now Pat. No. 11,840,476, which is a continuation of application No. 17/188,635, filed on Mar. 1, 2021, now Pat. No. 11,591,256, which is a continuation of application No. 16/310,133, filed as application No. PCT/US2017/039233 on Jun. 26, 2017, now abandoned.

(60) Provisional application No. 62/512,418, filed on May 30, 2017, provisional application No. 62/361,210, filed on Jul. 12, 2016, provisional application No. 62/354,271, filed on Jun. 24, 2016.

(51) Int. Cl.

| | |
|---|---|
| ***A61K 6/822*** | (2020.01) |
| ***A61K 6/824*** | (2020.01) |
| ***A61K 6/827*** | (2020.01) |
| ***A61K 6/833*** | (2020.01) |
| ***A61K 6/836*** | (2020.01) |
| ***C03B 32/02*** | (2006.01) |
| ***C03C 3/097*** | (2006.01) |
| ***C03C 4/00*** | (2006.01) |
| ***C03C 4/16*** | (2006.01) |
| ***C03C 14/00*** | (2006.01) |

(52) U.S. Cl.

CPC .............. *A61K 6/824* (2020.01); *A61K 6/827* (2020.01); *A61K 6/833* (2020.01); *A61K 6/836* (2020.01); *C03B 32/02* (2013.01); *C03C 3/097* (2013.01); *C03C 4/0021* (2013.01); *C03C 4/16* (2013.01); *C03C 10/0009* (2013.01); *C03C 14/004* (2013.01); *C03C 2214/04* (2013.01); *C03C 2214/20* (2013.01); *C03C 2214/30* (2013.01)

(56) References Cited

U.S. PATENT DOCUMENTS

| | | | |
|---|---|---|---|
| 3,809,543 A | 5/1974 | Gaskell et al. | |
| 5,173,453 A | 12/1992 | Beall et al. | |
| 5,176,961 A | 1/1993 | Crooker et al. | |
| 5,185,215 A | 2/1993 | Adams et al. | |
| 5,219,799 A | 6/1993 | Beall et al. | |
| 5,476,821 A | 12/1995 | Beall et al. | |
| 5,512,520 A | 4/1996 | Pfitzenmaier | |
| 5,925,180 A | 7/1999 | Frank et al. | |
| 9,101,439 B2 | 8/2015 | Ritzberger et al. | |
| 10,160,687 B2 | 12/2018 | Ritzberger et al. | |
| 2011/0092353 A1* | 4/2011 | Amin | C03C 10/16 501/3 |
| 2011/0256409 A1 | 10/2011 | Ritzberger et al. | |
| 2011/0257000 A1 | 10/2011 | Ritzberger et al. | |
| 2012/0246843 A1 | 10/2012 | Chambers et al. | |
| 2012/0309607 A1 | 12/2012 | Durschang et al. | |
| 2013/0323404 A1 | 12/2013 | Ritzberger et al. | |
| 2014/0194270 A1 | 7/2014 | Shiratori et al. | |
| 2014/0223965 A1 | 8/2014 | Ritzberger et al. | |
| 2014/0249016 A1 | 9/2014 | Durschang et al. | |
| 2015/0044474 A1 | 2/2015 | Beall et al. | |
| 2015/0246843 A1 | 9/2015 | Durschang et al. | |
| 2015/0274581 A1 | 10/2015 | Beall et al. | |
| 2016/0102010 A1 | 4/2016 | Beall et al. | |
| 2016/0106632 A1 | 4/2016 | Ritzberger et al. | |
| 2017/0119508 A1 | 5/2017 | Dittmer et al. | |
| 2017/0189143 A1 | 7/2017 | Wolz | |
| 2021/0179484 A1 | 6/2021 | Beall et al. | |

FOREIGN PATENT DOCUMENTS

| | | | |
|---|---|---|---|
| CN | 103011602 | A | 4/2013 |
| CN | 103945819 | A | 7/2014 |
| CN | 104108883 | A | 10/2014 |
| EP | 0916625 | A1 | 5/1999 |
| JP | 08-040744 | A | 2/1996 |
| JP | 2011-225441 | A | 11/2011 |
| JP | 2013-515659 | A | 5/2013 |
| KR | 10-2012-0073710 | A | 7/2012 |
| KR | 10-2012-0130088 | A | 11/2012 |

OTHER PUBLICATIONS

ASTM "Standard Test Method for Plane-Strain (Chevron-Notch) Fracture Toughness of Metallic Materials" E1304-97 pp. 1-12.

Chekhovskii V G et al: "Crystallization of Lithium Zirconium Silicate Glasses", Soviet Journal of Glass Physics and Chemistry. Fizika I Chimija Stekla, Maik Nauka/Interperiodica Publ, vol. 15, No. 3, May 1, 1989 (May 1, 1989), pp. 265-272.

Chinese Patent Application No. 201780046133.4, Office Action dated Jun. 11, 2021, 7 pages (English Translation Only), Chinese Patent Office.

Claussen et al; "Mechanical Properties of Sintered, in Situ-Reacted Mullite-Zirconia Composites" ; Journal of the American Ceramic Society—Discussions and Notes; vol. 63, No. 3-4; (1980) pp. 228-229.

Hannink et al; "Transformation Toughening in Zirconia-Containing Ceramics"; J. Am. Ceram. Society, Mar. 2000 , vol. 83, No. 3, pp. 461-487.

Huang et al; "Microstructure and Mechanical Properties of Zirconia-Toughened Lithium Disilicate Glass-Ceramic Composites"; Materials Chemistry And Physics 20i4; vol. 143, pp. 845-852.

International Search Report and Written Opinion Of The International Searching Aurthority; PCT/US2017/039281; Mailed Sep. 19, 2017, 14 Pages; European Patent Office.

Japanese Patent Application No. 2018-567225 Office Action dated Jun. 23, 2021, 8 pages (4 pages of English Translation and 4 pages of Original Document); Japanese Patent Office.

Korean Patent Application No. 10-2019-7002021, Notice of Allowance, dated Jan. 4, 2023, 6 pages (3 pages of English Translation and 3 pages of Original Copy); Korean Patent Office.

Montedo et al, "Low Thermal Expansion Sintered Lzsa Glass-Ceramics", American Ceramic Society Bulleting,2008 vol. 87, No. 7; pp. 34-40.

Novaes De Oliveira A P et al: "Properties of glasses belonging to the Li20—Zr02—Si02 system", Physics and Chemistry of Glasses, Society of Glass Technology, Sheffield, GB, vol. 39, No. 4, Aug. 1, 1998 (Aug. 1, 1998), pp. 213-221.

Oliveira et al: "Sintering and Crystallization of a Glass Powder in the LI20—ZR02—SI02 System", Journal of the American Ceramic Society, Blackwell Publishing, Malden, MA, US, vol. 81, No. 3, Mar. 1, 1998 (Mar. 1, 1998), pp. 777-780.

Sarno et al., "Toughening mechanisms for a zirconia-lithium aluminosilicate glass-ceramic", In Journal of Materials Science, vol. 30, 1995, pp. 4380-4388.

Schweiger et al; "Microstructure and Properties of a Composite System for Dental Applications Composed of Glass-Ceramics in The SiO2—Li2O—ZrO—P2O5 System And ZrO2-Ceramic (TZP)"; Journal of Materials Science; vol. 34; No. 19 (1999) pp. 4563-4572.

Taiwanese Patent Application No. 106121230 Summary of Official Letter dated Dec. 15, 2020; 4 Pages; (English Translation Only); Taiwanese Patent Office.

* cited by examiner

924 BMR 10kx 5kV

Si Ox%

ZIRCONIA-TOUGHENED GLASS CERAMICS

CROSS-REFERENCE TO RELATED APPLICATIONS

This application is a continuation of U.S. application Ser. No. 18/383,287 filed on Oct. 24, 2023, which is a continuation of U.S. application Ser. No. 18/096,315 filed on Jan. 12, 2023 now U.S. Pat. No. 11,840,476 granted on Dec. 12, 2023, which is a continuation of U.S. application Ser. No. 17/188,635 filed on Mar. 1, 2021, now U.S. Pat. No. 11,591,256 granted on Feb. 28, 2023, which is a continuation of U.S. application Ser. No. 16/310,133 filed on Dec. 14, 2018, which is a National Stage of International App. No. PCT/US2017/039233 filed on Jun. 26, 2017, which claims the benefit of priority of U.S. App. Nos. 62/512,418 filed on May 30, 2017; 62/361,210 filed on Jul. 12, 2016; and 62/354,271 filed on Jun. 24, 2016, the contents of each of which is relied upon and incorporated by reference herein in its entirety.

FIELD OF DISCLOSURE

The disclosure relates to glasses and glass ceramics. More particularly, the disclosure relates to glass ceramic-containing tetragonal zirconias along with the glasses that form these glass ceramics. Even more particularly, the disclosure relates to glass ceramic-containing tetragonal zirconias having high fracture toughness.

BACKGROUND

Transformation-toughened $ZrO_2$ ceramics are among the toughest and strongest of the engineering ceramics, and are typically produced via ceramic processing techniques such as hot pressing or sintering. In another approach, prefabricated $ZrO_2$ particles are dispersed in a matrix of either ceramic or glass. In this case, the $ZrO_2$ fraction of the final product is substantially lower than that of the pure ceramic material. Generally, these ceramics are generally monolithic-stabilized oxides, such as Ca, Mg, Ce or yttria-stabilized $ZrO_2$, where the principle phase of the monolith is $ZrO_2$.

In order to realize transformation toughening, it is necessary to obtain the tetragonal form of $ZrO_2$ in the as-made part. The tetragonal $ZrO_2$ phase transforms to the monoclinic phase under mechanical stress, which leads to toughening. However, $ZrO_2$ undergoes a thermal transition from tetragonal to monoclinic symmetry or structure at about 950° C. This can occur during processing of the materials, producing a material comprising the "transformed" monoclinic form. Presence of the monoclinic form in the as-made material does not offer the opportunity for subsequent transformation toughening.

SUMMARY

The present disclosure provides $ZrO_2$-toughened glass ceramics having high molar fractions of tetragonal $ZrO_2$ and a fracture toughness of greater than 2 $MPa \cdot m^{1/2}$. The glass ceramic may also include other secondary phases that may be beneficial for toughening or for strengthening. In some embodiments, strengthening may be achieved through an ion exchange process. Additional phases may also impart other properties or performance in the glass ceramic, such as decrease the coefficient of thermal expansion of the glass ceramic. A method of making such glass ceramics is also provided.

In an aspect (1), the disclosure provides a glass ceramic comprising at least two crystalline phases, the first crystalline phase comprising a $ZrO_2$ phase and the second crystalline phase comprising a lithium silicate phase, the glass ceramic further comprising a residual glass phase, whereby the resulting glass ceramic has an improved fracture toughness of from 1.8 to 10 $MPa \cdot m^{1/2}$ as measured by a chevron notch short bar method.

In another aspect (2), the disclosure provides the glass ceramic of aspect (1), wherein the first crystalline phase is a tetragonal $ZrO_2$ phase. In an aspect (3), the disclosure provides the glass ceramic of aspect (1) or (2), wherein the second crystalline phase is a lithium disilicate phase. In an aspect (4), the disclosure provides the glass ceramic of any of aspects (1)-(3), comprising the composition: 50-80 mol % $SiO_2$; 18-40 mol % $Li_2O$; 1.5-25 mol % $ZrO_2$, and greater than 0-5 mol % $P_2O_5$.

In an aspect (5), the disclosure provides the glass ceramic of any of aspects (1)-(4), wherein the at least two crystalline phases comprise a weight percent (wt %) of the total glass ceramic, measured as the (((weight of the at least two crystalline phases)/(total weight of the glass ceramic))*100), and wherein the at least two crystalline phases comprise from 30-98 wt % of the total glass ceramic. In an aspect (6), the disclosure provides the glass ceramic of any of aspects (1)-(5), wherein the at least two crystalline phases comprise from 60-95 wt % of the total glass ceramic. In an aspect (7), the disclosure provides the glass ceramic of any of aspects (1)-(6), wherein the tetragonal $ZrO_2$ comprises a weight percent (wt %) of the total $ZrO_2$ in the glass ceramic, measured as the (((weight of the tetragonal $ZrO_2$)/(total weight of $ZrO_2$ in the glass ceramic))*100), and wherein the tetragonal $ZrO_2$ comprises 40-95 wt % of $ZrO_2$ in the glass ceramic. In an aspect (8), the disclosure provides the glass ceramic of any of aspects (1)-(7), wherein the tetragonal $ZrO_2$ comprises a weight percent (wt %) of the total glass ceramic, measured as the (((weight of the tetragonal $ZrO_2$)/(total weight of the glass ceramic))*100), and wherein the tetragonal $ZrO_2$ phase comprises 5-25 wt % of the total glass ceramic. In an aspect (9), the disclosure provides the glass ceramic of any of aspects (1)-(8), wherein the tetragonal $ZrO_2$ comprises a weight percent (wt %) of the total crystalline phases of the glass ceramic, measured as the (((weight of the tetragonal $ZrO_2$)/(total weight of the crystalline phases of the glass ceramic))*100), and wherein tetragonal $ZrO_2$ phase may comprise 5-50 wt % of the total crystalline phases of the glass ceramic.

In an aspect (10), the disclosure provides the glass ceramic of any of aspects (1)-(9), wherein the tetragonal $ZrO_2$ crystals have an average crystal size from 0.1 to 10 μm along their longest dimension. In an aspect (11), the disclosure provides the glass ceramic of aspect (10), wherein the tetragonal $ZrO_2$ crystals have an average crystal size from 0.3 to 7 μm along their longest dimension. In an aspect (12), the disclosure provides the glass ceramic of aspect (11), wherein the tetragonal $ZrO_2$ crystals have an average crystal size from 0.5 to 4 μm along their longest dimension.

In an aspect (13), the disclosure provides the glass ceramic of any of aspects (1)-(12), wherein the lithium disilicate comprises a weight percent (wt %) of the total glass ceramic, measured as the (((weight of the lithium disilicate)/(total weight the glass ceramic))*100), and wherein the lithium disilicate comprises from 25-60 wt % of the total glass ceramic composition. In an aspect (14), the disclosure provides the glass ceramic of any of aspects (1)-(13), wherein the lithium disilicate comprises a weight percent (wt %) of the total crystalline phases of the glass ceramic, measured as the (((weight of the lithium disilicate)/(total weight of the crystalline phases of the glass ceramic))*100), and wherein lithium disilicate phase may comprise 5-50 wt % of the total crystalline phases of the glass ceramic. In an aspect (15), the disclosure provides the glass ceramic of any of aspects (1)-(14), wherein the lithium disilicate crystals have an average crystal size from 1 to 20 μm along their longest dimension. In an aspect (16), the disclosure provides the glass ceramic of aspect (15), wherein the lithium disilicate crystals have an average crystal size from 5 to 15 μm along their longest dimension.

In an aspect (17), the disclosure provides the glass ceramic of any of aspects (1)-(16), further comprising one or more additional crystalline phases. In an aspect (18), the disclosure provides the glass ceramic of aspect (17), wherein the one or more additional crystalline phases is selected from the group consisting of lithium aluminosilicate, cristobalite, beta-spodumene, lithiophosphate ($Li_3PO_4$), lithium orthophosphate, quartz solid solution, baddeleyite, lithium metasilicate ($Li_2SiO_3$), monoclinic zirconia, cubic zirconia, or (Na,Li)$ZrSi_6O_{18}$ or combinations thereof. In an aspect (19), the disclosure provides the glass ceramic of aspect (18), wherein the one or more additional crystalline phases is selected from the group consisting of monoclinic $ZrO_2$, lithium aluminosilicate, β-spodumene solid solution, β-quartz solid solution, or α-quartz or combinations thereof. In an aspect (20), the disclosure provides the glass ceramic of aspect (19), wherein the one or more additional crystalline phases is two or more phases selected from the group consisting of a monoclinic $ZrO_2$ and at least one of lithium aluminosilicate, β-spodumene solid solution, β-quartz solid solution, or α-quartz, wherein the monoclinic $ZrO_2$ is from >0-5 wt % of the glass ceramic.

In an aspect (21), the disclosure provides the glass ceramic of any of aspects (1)-(20), further comprising: 0-5 mol % $Al_2O_3$ and 0-5 mol % $Na_2O$. In an aspect (22), the disclosure provides the glass ceramic of any of aspects (1)-(21), further comprising: 0-14 mol % $R_2O$; 0-10 mol % MO; 0-5 mol % TMO; and 0-5 mol % REO. In an aspect (23), the disclosure provides the glass ceramic of any of aspects (1)-(22), comprising: 55-70 mol % $SiO_2$; 18-30 mol % $Li_2O$; 4-20 mol % $ZrO_2$; and 0.2-5 mol % $P_2O_5$. In an aspect (24), the disclosure provides the glass ceramic of any of aspects (1)-(23) comprising: 58-69 mol % $SiO_2$; 25-36 mol % $Li_2O$; 6-15 mol % $ZrO_2$; >0-5 mol % $Al_2O_3$; 0-5 mol % $B_2O_3$; 0.2-3 mol % $P_2O_5$; 0-8 mol % MO; 0-5 mol % TMO; and 0-5 mol % REO. In an aspect (25), the disclosure provides the glass ceramic of any of aspects (1)-(24) further comprising >0-5 mol % REO. In an aspect (26), the disclosure provides the glass ceramic of aspect (25), wherein REO comprises $Y_2O_3$ and $Y_2O_3$ (mol %)/$ZO_2$ (mol %)<0.2. In an aspect (27), the disclosure provides the glass ceramic of any of aspects (1)-(26), wherein the glass ceramic is free of $Rb_2O$ and $Cs_2O$. In an aspect (28), the disclosure provides the glass ceramic of any of aspects (1)-(27), further comprising >0-5 mol % $TiO_2$. In an aspect (29), the disclosure provides the glass ceramic of any of aspects (1)-(28), further comprising >0-3 mol % ZnO.

In an aspect (30), the disclosure provides the glass ceramic of any of aspects (1)-(29), further comprising >0-4 mol % of a color component. In an aspect (31), the disclosure provides the glass ceramic of aspect (30), wherein the color component comprises $Fe_2O_3$, $V_2O_5$, $Cr_2O_3$, $MnO_2$, NiO, CuO, $Co_3O_4$ and combinations thereof. In an aspect (32), the disclosure provides the glass ceramic of any of aspects (1)-(31), wherein the glass ceramic exhibit a color presented in CIELAB color space coordinates: a*=from about −1 to about +3; b*=from about −7 to about +3; and L*>85. In an aspect (33), the disclosure provides the glass ceramic of any of aspects (1)-(32), wherein a*=from about −1 to about 0; b*=from about −2 to about 0; and L*>88. In an aspect (34), the disclosure provides the glass ceramic of any of aspects (1)-(31), wherein the glass ceramic exhibit a color presented in CIELAB color space coordinates: a*=from about −1 to about 1; b*=from about −4 to about 1; and L*<60. In an aspect (35), the disclosure provides the glass ceramic of aspect (34), wherein a*=from about −1 to about 1; b*=from about −1 to about 1; and L*<40. In an aspect (36), the disclosure provides the glass ceramic of any of aspects (1)-(35), wherein the glass ceramic has a fracture toughness of from 2 to 10 MPa·$m^{1/2}$ as measured by Chevron notch short bar methods. In an aspect (37), the disclosure provides the glass ceramic of any of aspects (1)-(36), wherein the glass ceramic further comprises an ion exchanged layer, the ion exchanged layer having a depth of compression of at least 10 μm. In an aspect (38), the disclosure provides the glass ceramic of aspect (37), wherein the ion exchanged layer has a depth of compression of at least 30 μm. In an aspect (39), the disclosure provides the glass ceramic of aspect (37) or (38), wherein the surface compression of the glass ceramic is from 350 MPa to 800 MPa.

In an aspect (40), the disclosure provides an article comprising the glass ceramic of any of aspects (1)-(39). In an aspect (41), the disclosure provides the article of aspect (40), wherein the article comprises a portion of a housing for a consumer electronic device, the consumer electronic device comprising the housing and electrical components provided at least partially internal to the housing. In an aspect (42), the disclosure provides the article of aspect (40), wherein the glass ceramic forms at least a portion of a dental composite, a dental restorative, or a dental article. In an aspect (43), the disclosure provides the article of aspect (42), wherein the dental article is one of a filling, a bridge, a splint, a crown, a partial a crown, a denture, a tooth, a jacket, an inlay, an onlay, a facing, a veneer, a facet, an implant, a cylinder, an abutment, or a connector.

In an aspect (44), the disclosure provides a method of making the glass ceramic of any of aspects (1)-(39), the method comprising the steps of: a. providing a precursor glass material, the precursor material comprising $SiO_2$, $Li_2O$, $ZrO_2$ and $P_2O_5$; b. ceramming the precursor material to form the glass ceramic, wherein ceramming comprises heating the precursor material at a first temperature for a first time period of from about 15 minutes to about 3 hours, followed by heating to a second temperature for a second time period of from about 0.5 hour to 5 hours, wherein the first temperature is in a range from about 600° C. to about 850° C. and the second temperature is in a range from about 725° C. to about 1000° C.

In an aspect (45), the disclosure provides a method of making the glass ceramic of aspect (44), wherein the precursor glass material comprises: 50-80 mol % $SiO_2$; 18-40 mol % $Li_2O$; 3-25 mol % $ZrO_2$; and greater than 0-5 mol % $P_2O_5$. In an aspect (46), the disclosure provides a method of making the glass ceramic of aspect (45), wherein the precursor material further comprises: 0-5 mol % $Al_2O_3$ and 0-5 mol % $Na_2O$. In an aspect (47), the disclosure provides a method of making the glass ceramic of aspect (45) or (46), wherein the precursor material further comprises: 0-14 mol % $R_2O$; 0-10 mol % MO; 0-5 mol % TMO; and 0-5 mol %

REO. In an aspect (48), the disclosure provides a method of making the glass ceramic of any of aspects (44)-(47), wherein the precursor material comprises: 55-70 mol % $SiO_2$; 18-30 mol % $Li_2O$; 4-20 mol % $ZrO_2$; and 0.2-5 mol % $P_2O_5$. In an aspect (49), the disclosure provides a method of making the glass ceramic of any of aspects (44)-(48), wherein the precursor material comprises: 58-69 mol % $SiO_2$; 25-36 mol % $Li_2O$; 6-15 mol % $ZrO_2$; >0-5 mol % $Al_2O_3$; 0-5 mol % $B_2O_3$; 0.2-3 mol % $P_2O_5$; 0-8 mol % MO; 0-5 mol % TMO; and 0-5 mol % REO.

In an aspect (50), the disclosure provides a method of making the glass ceramic of any of aspects (44)-(49), wherein the precursor material further comprises >0-5 mol % REO. In an aspect (51), the disclosure provides a method of making the glass ceramic of aspect (50), wherein REO comprises $Y_2O_3$ or $CeO_2$. In an aspect (52), the disclosure provides a method of making the glass ceramic of any of aspects (44)-(51), wherein the precursor material is free of $Rb_2O$ and $Cs_2O$. In an aspect (53), the disclosure provides a method of making the glass ceramic of any of aspects (44)-(52), wherein the precursor material further comprises >0-5 mol % $TiO_2$. In an aspect (54), the disclosure provides a method of making the glass ceramic of any of aspects (44)-(53), wherein the precursor material further comprises >0-3 mol % ZnO. In an aspect (55), the disclosure provides a method of making the glass ceramic of any of aspects (44)-(54), wherein the precursor material further comprises >0-4 mol % of a color component. In an aspect (56), the disclosure provides a method of making the glass ceramic of any of aspects (44)-(55), wherein the color component comprises $Fe_2O_3$, $V_2O_5$, $Cr_2O_3$, $MnO_2$, NiO, CuO, NiO, $Co_3O_4$ and combinations thereof.

In an aspect (57), the disclosure provides a method of making the glass ceramic of any of aspects (44)-(56), wherein the first time period is from about 15 minutes to about 1 hour. In an aspect (58), the disclosure provides a method of making the glass ceramic of any of aspects (44)-(57), wherein the second time period is from about 0.5 hour to about 2 hours. In an aspect (59), the disclosure provides a method of making the glass ceramic of any of aspects (44)-(58), wherein the precursor material comprises a precursor glass. In an aspect (60), the disclosure provides a method of making the glass ceramic of any of aspects (44)-(59), wherein the precursor material further includes grinding the precursor glass to a precursor glass powder. In an aspect (61), the disclosure provides a method of making the glass ceramic of any of aspects (44)-(60), further comprising the step of sintering and ceramming the precursor glass powder. In an aspect (62), the disclosure provides a method of making the glass ceramic of any of aspects (44)-(61), further comprising sintering the glass ceramic. In an aspect (63), the disclosure provides a method of making the glass ceramic of any of aspects (44)-(62), further comprising hot pressing the glass ceramic. In an aspect (64), the disclosure provides a method of making the glass ceramic of any of aspects (44)-(63), further comprising machining or shaping the glass precursor material prior to heating the precursor material at the first temperature. In an aspect (65), the disclosure provides a method of making the glass ceramic of any of aspects (44)-(64), further comprising machining or shaping the glass precursor material following heating the precursor material at the first temperature and prior to heating the precursor material at the second temperature.

In an aspect (66), the disclosure provides the glass ceramic of any of aspects (1)-(43) producible by the process: a. providing a precursor material, the precursor material comprising $SiO_2$, $L_2O$, $ZrO_2$, and $P_2O_5$; b. ceramming the precursor material to form the glass ceramic, wherein ceramming comprises heating the precursor material at a first temperature for a first time period of from about 15 minutes to about 3 hours, followed by heating to a second temperature for a second time period of from about 0.5 hour to 5 hours, wherein the first temperature is in a range from about 600° C. to about 850° C. and the second temperature is in a range from about 725° C. to about 1000° C.

In an aspect (67), the disclosure provides the glass ceramic of aspect (66), wherein the precursor glass material comprises: 50-80 mol % $SiO_2$; 18-40 mol % $Li_2O$; 3-25 mol % $ZrO_2$; and greater than 0-5 mol % $P_2O_5$.

These and other aspects, advantages, and salient features will become apparent from the following detailed description, the accompanying drawings, and the appended claims.

BRIEF DESCRIPTION OF THE DRAWINGS

Referring to the drawings in general, it will be understood that the illustrations are for the purpose of describing particular embodiments and are not intended to limit the disclosure or appended claims thereto. The drawings are not necessarily to scale, and certain features and certain views of the drawings may be shown exaggerated in scale or in schematic in the interest of clarity and conciseness.

FIG. 3B shows the silicon present in the material, FIG. 3C shows the zirconia, and FIG. 3D shows the phosphorous.

FIG. 4A shows the phase assemblage for Example 8, FIG. 4B for Example 14, FIG. 4C for Example 40, and FIG. 4D for Example 44. All examples were cerammed at 750° C. for 2 hours, then 875° C. for 4 hours, except Example 44 which was cerammed at 750° C. for 2 hours, then 850° C. for 4 hours.

DETAILED DESCRIPTION

Figure 1A:
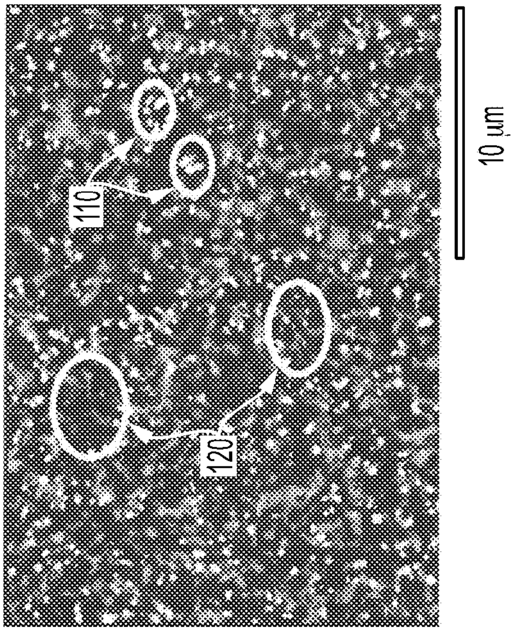
FIG. 1A is a scanning electron microscopy (SEM) image of a glass ceramic material that was cerammed by heating at 750° C. for 2 hours and then heating at 900° C. for 4 hours.

In the following description, like reference characters designate like or corresponding parts throughout the several views shown in the figures. It is also understood that, unless otherwise specified, terms such as "top," "bottom," "outward," "inward," and the like are words of convenience and are not to be construed as limiting terms. In addition, whenever a group is described as comprising at least one of a group of elements and combinations thereof, it is understood that the group may comprise, consist essentially of, or consist of any number of those elements recited, either individually or in combination with each other. Similarly, whenever a group is described as consisting of at least one of a group of elements or combinations thereof, it is understood that the group may consist of any number of those elements recited, either individually or in combination with each other. Unless otherwise specified, a range of values, when recited, includes both the upper and lower limits of the range as well as any ranges therebetween. As used herein, the indefinite articles "a," "an," and the corresponding definite article "the" mean "at least one" or "one or more," unless otherwise specified. It also is understood that the various features disclosed in the specification and the drawings can be used in any and all combinations.

Where a range of numerical values is recited herein, comprising upper and lower values, unless otherwise stated in specific circumstances, the range is intended to include the endpoints thereof, and all integers and fractions within the range. It is not intended that the scope of the claims be limited to the specific values recited when defining a range. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. Finally, when the term "about" is used in describing a value or an end-point of a range, the disclosure should be understood to include the specific value or end-point referred to. When a numerical value or end-point of a range does not recite "about," the numerical value or end-point of a range is intended to include two embodiments: one modified by "about," and one not modified by "about."

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. It is noted that the terms "substantially" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. Thus, a glass that is "free of $Al_2O_3$" is one in which $Al_2O_3$ is not actively added or batched into the glass, but may be present in very small amounts as a contaminant (e.g., 500, 400, 300, 200, or 100 parts per million (ppm) or less or).

Unless otherwise specified, all compositions are expressed in terms of mole percent (mol %). Compositional ranges of crystalline materials in the glass ceramic are expressed in terms of weight percent (wt %) unless otherwise specified. Coefficients of thermal expansion (CTE) are expressed in terms of $10^{-7}$/° C. and represent a value measured over a temperature range from 20° C. to 300° C., unless otherwise specified. The density in terms of grams/$cm^3$ was measured via the Archimedes method (ASTM C693).

Vickers crack initiation thresholds described herein are determined by applying and then removing an indentation load to the glass surface at a rate of 0.2 mm/min. The indenter uses a standard 136° tip angle on a diamond indenter. The maximum indentation load is held for 10 seconds. The indentation cracking threshold is defined at the indentation load at which 50% of 10 indents exhibit at least one radial/median crack emanating from the corners of the indent impression. The maximum load is increased until the threshold is met for a given glass ceramic and/or the precursor glass. All indentation measurements are performed at room temperature in 50% relative humidity.

Fracture toughness values described herein as measured by chevron notch short bar methods known in the art and described in ASTM procedure E1304-97 (2014), entitled "Standard Test Method for Plane-Strain (Chevron-Notch) Fracture Toughness of Metallic Materials." The contents of ASTM E1304-97 (2014) are incorporated herein by reference in their entirety. The test method involves application of a load to the mouth of a chevron-notched specimen to induce an opening displacement of the specimen mouth. Fracture toughness measured according to this method is relative to a slowly advancing steady-state crack initiated at a chevron notch and propagating in a chevron-shaped ligament.

Glass Ceramics and Glass Ceramic Precursors

When a glass is converted into a glass-ceramic, portions of the glass crystallize while other portions may remain in a residual glass phase (e.g., amorphous, non-crystalline). As used herein, the term "glass ceramic" refers to a material comprising at least one crystalline phase and at least one residual glass phase. The amount of material in a crystalline phase or in crystalline phases is measured in wt %. The weight fraction ratio of the crystalline phases may be determined by methods known in the art, such as x-ray diffraction methods including Rietveld refinement. In some embodiments, a glass ceramic is a material comprising at least 30%, 50%, 60%, 70%, 75%, 80%, 85%, 90%, 95%, 97%, 98%, 99% or greater than 99% w/w at least one crystalline phase, with the remaining volume comprising a glass phase. In some embodiment, the material comprises from 50-98% glass ceramic phase, 60-98% glass ceramic phase, 70-98% glass ceramic phase, 80-98% glass ceramic phase, 80-95% glass ceramic phase, or 60-90% glass ceramic phase. The terms "glass ceramic article" and "glass ceramic articles" are used in their broadest sense to include any object made wholly or partly of glass ceramic. The terms "ceram" and "ceramming," as used herein, refer to a heat treatment (or heat treatments) or other process(es) used to convert a precursor glass into a glass ceramic.

The glass ceramics described herein include crystalline structures that can be understood via crystallography and known crystal systems. As used herein the terms "tetragonal $ZrO_2$," "tetragonal zirconia," and "t-$ZrO_2$" are used interchangeably and refer to crystalline $ZrO_2$ having a tetragonal crystal system; the terms "monoclinic $ZrO_2$," "monoclinic zirconia," and "m-$ZrO_2$" are used interchangeably and refer to crystalline $ZrO_2$ having a monoclinic crystal system; and the term "cubic $ZrO_2$" is used interchangeably and refer to crystalline $ZrO_2$ having a cubic crystal system as understood in chemical crystallography. "Lithium silicate" phase may comprise lithium disilicates, monosilicates, and metasilicates. Additional crystalline structures may be present in the precursor glass or glass ceramic phases of the materials. For example, lithium disilicate glass ceramic phases may have orthorhombic or other crystal systems.

A first aspect comprises zirconia-containing precursor glasses and glass ceramics made from the precursor glasses. The glass ceramics made from these zirconia-containing precursor glasses are zirconia-toughened glass ceramics having high weight fractions of tetragonal $ZrO_2$. While not being bound by theory, it is believed that the high levels of tetragonal $ZrO_2$ allow for the glass ceramic to undergo phase transformation from tetragonal $ZrO_2$ to monoclinic $ZrO_2$, greatly improving the materials fracture toughness. Support for this theory is seen in the fact that ground powders made from these materials see increases in the amount of monoclinic $ZrO_2$ present. In some embodiments, the crystalline zirconia-containing glass ceramics may also comprise a lithium silicate phase. In some embodiments, the crystalline zirconia phase is tetragonal zirconia and the lithium silicate phase is lithium disilicate.

The precursor glass is capable of dissolving a large amount (generally, greater than about 10 wt %) of $ZrO_2$ without crystallizing upon cooling from the glass pour. Lithium and/or magnesium silicate melts with relatively low alumina contents generally have high $ZrO_2$ solubility. When the precursor glass is subjected to a prescribed heat treatment, dissolved $ZrO_2$ is crystallized and precipitated out primarily as the tetragonal $ZrO_2$ phase with, in some embodiments, less than 5 wt % monoclinic $ZrO_2$ relative to the total $ZrO_2$.

Figure 1B:
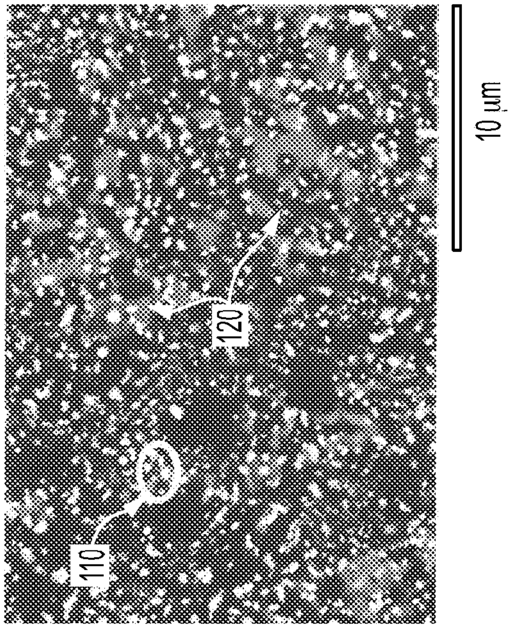
FIG. 1B is a SEM image of a glass ceramic material that was cerammed by heating at 800° C. for 2 hours and then heating at 900° C. for 4 hours.

The glass ceramics described herein comprise a tetragonal $ZrO_2$ phase, a crystalline lithium disilicate ($Li_2Si_2O_5$) phase, optionally a lithium aluminosilicate phase and a residual glass phase. FIGS. 1A and 1B provide example micrographs of embodied glass ceramics comprising a tetragonal $ZrO_2$ phase and a crystalline lithium disilicate ($Li_2Si_2O_5$) phase. The tetragonal $ZrO_2$ phase, in some embodiments, may comprise a significant portion (40-95 wt %, 40-90 wt %, or 50-80 wt %) the $ZrO_2$ present in the glass ceramic. In some embodiments, the tetragonal $ZrO_2$ phase may comprise 5-25 wt % of the total glass ceramic composition (([weight tetragonal $ZrO_2$]/[weight of glass ceramic])*100). In some embodiments, the tetragonal $ZrO_2$ phase may comprise 5-60 wt %, 5-50 wt %, 5-40 wt %, 5-30 wt %, or 10-35 wt % of the total crystalline phase of the glass ceramic (([weight of tetragonal $ZrO_2$]/[weight of all crystalline phases])*100). The tetragonal $ZrO_2$ phase may, in some embodiments, be dispersed throughout the residual glass phase. In other embodiments, the crystalline t-$ZrO_2$ phase "decorates" or is near or in contact with the lithium disilicate phase such that the t-$ZrO_2$ and lithium disilicate phases may synergistically interact to provide improved material properties. In some embodiments, the average crystal size along the longest dimension for crystals of tetragonal $ZrO_2$ is from 0.1 to 10 μm, 0.3 to 7 μm, 0.5 to 4 μm, 0.8 to 3 μm, or 0.5 to 3 μm.

The glass ceramic further comprises a lithium disilicate phase. In some embodiments, the lithium disilicate phase comprises about 25 to about 60 wt % of the total glass ceramic composition. In some embodiments, the tetragonal $ZrO_2$ and lithium disilicate phases comprise 60-95 wt % of the total glass ceramic. In some embodiments, the lithium disilicate phase may comprise 5-50 wt % of the total crystalline phase of the glass ceramic. The lithium disilicate crystals may have a lath-like structure, with an aspect ratio of from about 1.5:1 to 12:1, 2:1 to 8:1 or greater than 2:1. In some embodiments, the average crystal size along the longest dimension for crystals of lithium disilicate is at least 2 μm, 5 μm, 8 μm, or 10 μm or from 1 to 20 μm, 2 to 15 μm, 5 to 20 μm, 5 to 15 μm, 5 to 12 μm, 2 to 12 μm, 1 to 12 μm, 8 to 20 μm, or 10 to 20 μm.

In some embodiments, the glass ceramic further comprises one or more additional phases, such as lithium metasilicate, cubic zirconia, monoclinic $ZrO_2$, lithium aluminosilicate, β-spodumene solid solution, β-quartz solid solution, cristobalite, lithiophosphate, zekzerite, quartz solid solution, baddeleyite, lithium orthophosphate, $(Na,Li)ZrSi_6O_{18}$, or α-quartz phase or combinations thereof. In some embodiments, the additional phases comprise, in total, about 0-25 wt % of the glass ceramic.

The glass phase, in some embodiments, may comprise 1-50 wt %, 2-50 wt %, 3-50 wt %, 5-40 wt %, 5-30 wt %, 5-20 wt %, 3-10 wt %, or 5-50 wt % of the total glass ceramic composition.

In some embodiments, the tetragonal $ZrO_2$/lithium disilicate glass ceramic and/or the precursor glass used to form the glass ceramic comprises at least 3 mol % $ZrO_2$ and 18 to 40 mol % $Li_2O$, 19 to 37 mol % $Li_2O$, 25 to 35 mol % $Li_2O$, or 30 to 35 mol % $Li_2O$. In some embodiments, the glass ceramic and/or the precursor glass used to form the glass ceramic may comprise additional components. In some embodiments, additionally comprises 0 to 7 mol % $Al_2O_3$, 0 to 5 mol % $Al_2O_3$, 0 to 4 mol % $Al_2O_3$, 0 to 3 mol % $Al_2O_3$, >0 to 7 mol % $Al_2O_3$, >0 to 5 mol % $Al_2O_3$, >0 to 4 mol % $Al_2O_3$, >0 to 3 mol % $Al_2O_3$, 0.5 to 7 mol % $Al_2O_3$, 0.5 to 5 mol % $Al_2O_3$, 0.5 to 4 mol % $Al_2O_3$, or 0.5 to 3 mol % $Al_2O_3$.

In some embodiments, the glass ceramic may further include at least one of crystalline cubic $ZrO_2$ or monoclinic $ZrO_2$ phases. In some embodiments, the glass ceramic may comprise a monoclinic $ZrO_2$ phase. In such instances, the ratio of weight fraction (or weight percentage) of tetragonal zirconia to that of monoclinic zirconia is at least about 8:1 (i.e., tetragonal-$ZrO_2$ (wt %)/monclinic-$ZrO_2$ (wt %))≥8); in some embodiments, at least about 10:1 (tetragonal-$ZrO_2$ (wt %)/monclinic-$ZrO_2$ (wt %))≥10); in other embodiments, at least about 15 (tetragonal-$ZrO_2$ (wt %)/monclinic-$ZrO_2$ (wt %))≥15); and in still other embodiments, at least about 20 (tetragonal-$ZrO_2$ (wt %)/monclinic-$ZrO_2$ (wt %))≥20). In some embodiments the amount of monclinic-$ZrO_2$ in the glass ceramic is from 0 to 5 wt %, >0 to 5 wt %, 0 to 3 wt %, 0 to 1 wt %, >0 to 3 wt %, or >0 to 1 wt %. The weight fraction ratio of the tetragonal to monoclinic zirconia phases may be determined by those x-ray diffraction methods, such as Rietveld refinement, known in the art.

In some embodiments, the glass ceramic and/or the precursor glass used to form the glass ceramic comprises a combination of $SiO_2$, $Li_2O$, $ZrO_2$, and optionally, $Al_2O_3$, alkali oxides, alkaline earth oxides, and rare earth oxides. For example, embodiments may comprise from 50 mol % to 75 mol % $SiO_2$ (50 mol %≤$SiO_2$≤75 mol %); from 18 mol % to 40 mol % $Li_2O$ (18 mol %≤$Li_2O$≤40 mol % $Li_2O$); from 3 mol % to 17 mol % $ZrO_2$ (3 mol %≤$ZrO_2$≤15 mol %); from 0 mol % to 5 mol % $Al_2O_3$ (0 mol %≤$Al_2O_3$≤5 mol %); from 0 mol % to 5 mol % $Na_2O$ (0 mol %≤$Na_2O$≤5 mol %); from greater than 0 mol % to 14 mol % $R_2O$ (0 mol %<$R_2O$≤14 mol %), where R is the sum of the alkali metals Na, K, and Cs (not Li); from 0 mol % to 5 mol % of at least one alkaline earth oxide (RO; R=Mg, Sr, Ca, Ba) (0 mol %≤RO≤5 mol %); from 0 mol % to 5 mol % of at least one transition metal oxide ("TMO") (oxids of metals in groups IVB-VIII, IB, and IIB, or 4-12 in the periodic table; e.g., Zn, Ti, Fe, etc.) (0 mol %≤RO≤5 mol %); and from 0 mol % to 5 mol % of at least one rare earth oxide ("REO") (oxides of scandium, yttrium, and the lanthanides) (0 mol %≤REO≤5 mol %). Additional aspects of the various constituents that can make up the embodied compositions are detailed below.

$SiO_2$, along with $Al_2O_3$, $B_2O_3$, $P_2O_5$, $ZrO_2$ and $SnO_2$, are network formers when present in the glass ceramic and/or the precursor glass. $SiO_2$, which is the largest oxide component of the glass ceramic and/or the precursor glass, may be included to provide high temperature stability and chemical durability. In some embodiments, the glass ceramic and/or the precursor glass can comprise from 50 to 75 mol % $SiO_2$. In some embodiments, the glass ceramic and/or the precursor glass can comprise from 55 to 70 mol % $SiO_2$. In some embodiments, the glass ceramic and/or the precursor glass can comprise from 57 to 65 mol % $SiO_2$. In some embodiments, the glass ceramic and/or the precursor glass can comprise from 57 to 70 mol % $SiO_2$. In some embodiments, the glass ceramic and/or the precursor glass can comprise 50 to 75 mol %, 50 to 70 mol %, 50 to 65 mol %, 50 to 60 mol %, 55 to 75 mol %, 57 to 70 mol %, 57 to 65 mol %, 55 to 70 mol %, or 55 to 65 mol % $SiO_2$. In some embodiments, the glass ceramic and/or the precursor glass comprises 50, 51, 52, 53, 54, 55, 56, 57, 58, 59, 60, 61, 62, 63, 64, 65, 66, 67, 68, 69, 70, 71, 72, 73, 74, or 75 mol % $SiO_2$.

$Li_2O$ may provide the basis for the lithium disilicate phase. In some embodiments, the glass ceramic and/or the precursor glass can comprise from 18 to 40 mol % $Li_2O$. In some embodiments, the glass ceramic and/or the precursor glass can comprise 18 to 30 mol % $Li_2O$. In some embodiments, the glass ceramic and/or the precursor glass can comprise 25 to 36 mol % $Li_2O$. In some embodiments, the glass ceramic and/or the precursor glass can comprise 30 to 35 mol % $Li_2O$. In some embodiments, the glass ceramic and/or the precursor glass can comprise from 18 to 40 mol %, 18 to 36 mol %, 18 to 30 mol %, 18 to 25 mol %, 20 to 40 mol %, 20 to 36 mol %, 20 to 30 mol %, 20 to 25 mol %, 25 to 40 mol %, 25 to 36 mol %, 25 to 30 mol %, 30 to 40 mol %, 30 to 36 mol %, or 36 to 40 mol %. In some embodiments, the glass ceramic and/or the precursor glass can comprise 18, 19, 20, 21, 22, 23, 24, 25, 26, 27, 28, 29, 30, 31, 32, 33, 34, 35, 36, 37, 38, 39, or 40 mol % $Li_2O$.

Zirconium dioxide or zirconia, $ZrO_2$, is the primary component of the tetragonal and other crystalline $ZrO_2$ phases. In some embodiments, the glass ceramic and/or the precursor glass can comprise at least 3 mol % $ZrO_2$ or, in some embodiments, from 3 to 25 mol % $ZrO_2$. In some embodiments, the glass ceramic and/or the precursor glass can comprise from 4 to 20 mol % $ZrO_2$. In some embodiments, the glass ceramic and/or the precursor glass can comprise from 6 to 15 mol % $ZrO_2$. In some embodiments, the glass ceramic and/or the precursor glass can comprise from 3 to 25 mol %, 3 to 20 mol %, 3 to 18 mol %, 3 to 15 mol %, 3 to 12 mol %, 3 to 10 mol %, 3 to 8 mol %, 4 to 25 mol %, 4 to 20 mol %, 4 to 18 mol %, 4 to 15 mol %, 4 to 12 mol %, 4 to 10 mol %, 4 to 8 mol %, 6 to 25 mol %, 6 to 20 mol %, 6 to 18 mol %, 6 to 15 mol %, 6 to 12 mol %, 6 to 10 mol %, $ZrO_2$. In some embodiments, the glass ceramic and/or the precursor glass can comprise 3, 4, 5, 6, 7, 8, 9, 10, 11, 12, 13, 14, 15, 16, 17, 18, 19, 20, 21, 22, 23, 24, or 25 mol % $ZrO_2$.

$Al_2O_3$ may influence the structure of the precursor glass and/or the glass ceramic and, additionally, lower the liquidus temperature and coefficient of thermal expansion, or enhance the strain point. In some embodiments, the glass ceramic and/or the precursor glass can comprise from 0 to 5 mol % $Al_2O_3$. In some embodiments, the glass ceramic and/or the precursor glass can comprise from >0 to 5 mol % $Al_2O_3$. In some embodiments, the glass ceramic and/or the precursor glass can comprise from about 0 to 3 mol % $Al_2O_3$ or >0 to 3 mol % $Al_2O_3$. In some embodiments, the glass ceramic and/or the precursor glass can comprise from 1 to 4 mol % $Al_2O_3$. In some embodiments, the glass ceramic and/or the precursor glass can comprise from 0 to 5 mol %, 0 to 4 mol %, 0 to 3 mol %, 0 to 2 mol %, >0 to 5 mol %, >0 to 4 mol %, >0 to 3 mol %, >0 to 2 mol %, 1 to 5 mol %, 1 to 4 mol %, or 1 to 3 mol % $Al_2O_3$. In some embodiments, the glass ceramic and/or the precursor glass can comprise about 0, >0, 1, 2, 3, 4, or 5 mol % $Al_2O_3$.

Without being bound by theory, it is believed that limiting the content of $B_2O_3$ in the glasses and glass ceramics described herein to 0 to 5 wt % helps provide a durable glass ceramic. In some embodiments, the glass ceramic and/or the precursor glass can comprise from 0 to 5 mol % $B_2O_3$. In some embodiments, the glass ceramic and/or the precursor glass can comprise from >0 to 5 mol % $B_2O_3$. In some embodiments, the glass ceramic and/or the precursor glass can comprise from about 0 to 3 mol % $B_2O_3$ or >0 to 3 mol % $B_2O_3$. In some embodiments, the glass ceramic and/or the precursor glass can comprise from 1 to 4 mol % $B_2O_3$. In some embodiments, the glass ceramic and/or the precursor glass can comprise from 0 to 5 mol %, 0 to 4 mol %, 0 to 3 mol %, 0 to 2 mol %, >0 to 5 mol %, >0 to 4 mol %, >0 to 3 mol %, >0 to 2 mol %, 1 to 5 mol %, 1 to 4 mol %, or 1 to 3 mol % $B_2O_3$. In some embodiments, the glass ceramic and/or the precursor glass can comprise about 0, >0, 1, 2, 3, 4, or 5 mol % $B_2O_3$.

Phosphorous pentoxide, $P_2O_5$, may be present in order to stabilize the tetragonal $ZrO_2$. In some embodiments, the glass ceramic and/or the precursor glass can comprise from >0 to 5 mol % $P_2O_5$. In some embodiments, the glass ceramic and/or the precursor glass can comprise from 0.2 to 5 mol % $P_2O_5$. In some embodiments, the glass ceramic and/or the precursor glass can comprise from about >0 to 3 mol % $P_2O_5$ or 0.2 to 3 mol % $P_2O_5$. In some embodiments, the glass ceramic and/or the precursor glass can comprise from 1 to 4 mol % $P_2O_5$. In some embodiments, the glass ceramic and/or the precursor glass can comprise from 0.2 to 5 mol %, 0.2 to 4 mol %, 0.2 to 3 mol %, 0.2 to 2 mol %, >0 to 5 mol %, >0 to 4 mol %, >0 to 3 mol %, >0 to 2 mol %, 1 to 5 mol %, 1 to 4 mol %, or 1 to 3 mol % $P_2O_5$. In some embodiments, the glass ceramic and/or the precursor glass can comprise about 0, >0, 1, 2, 3, 4, or 5 mol % $P_2O_5$.

Rare earth oxides may be present in order to stabilize the tetragonal $ZrO_2$. In some embodiments, the glass ceramic and/or the precursor glass comprises from 0 mol % to 5 mol % of at least one rare earth oxide (REO; i.e., oxides of scandium, yttrium, and the lanthanides) (0 mol %≤REO≤5 mol %). In some embodiments, the glass ceramic and/or the precursor glass comprises from greater than 0 mol % to 5 mol % of at least one rare earth oxide (REO; i.e., oxides of scandium, yttrium, and the lanthanides) (0 mol %<REO≤5 mol %), where 'greater than 0' means any positive value, such as 0.001 mol %. The glass ceramic and/or the precursor glass may, in some embodiments, comprise from 0 mol % to 3 mol % or from greater than 0 mol % to 2 mol % $Y_2O_3$ (0 mol %≤$Y_2O_3$≤3 mol % or 0 mol %<$Y_2O_3$≤2 mol %). In some embodiments, the ratio of $Y_2O_3$ (mol %)/$ZrO_2$ (mol %) is less than 0.2, 0.15, 0.1, 0.05, or 0.1. In some embodiments, the glass ceramic and/or the precursor glass comprises from 0 to 5 mol %, >0 to 5 mol %, 1 to 5 mol %, 2 to 5 mol %, 0 to 4 mol %, 0 to 3 mol %, 0 to 2 mol %, 0 to 1 mol %, >0 to 4 mol %, >0 to 3 mol %, >0 to 2 mol %, or >0 to 1 mol %, 0 to about 0.5 mol %, 0 to about 0.1 mol %, 0 to about 0.05 mol %, or 0 to about 0.01 mol % $CeO_2$.

Non-lithium alkali oxides may also be present in the glass ceramic and/or the precursor glass. In some embodiments, the glass ceramic and/or the precursor glass comprises from 0 mol % to about 14 mol % $R_2O$ (0 mol %<$R_2O$≤14 mol %), where R is the sum of the alkali metals Na, K, Cs, and Rb (not Li), in the glass ceramic and/or the precursor glass. In some embodiments, the glass ceramic and/or the precursor glass can comprise from 0 to 10 mol % or 0 to 8 mol % $R_2O$. In some embodiments, the glass ceramic and/or the precursor glass can comprise from >0 to 14, >0 to 10, or >0 to 8 mol % $R_2O$. In some embodiments, the glass ceramic and/or the precursor glass can comprise 0.5 to 4 mol % $R_2O$. In some embodiments, the glass ceramic and/or the precursor glass can comprise from 0 to 14 mol %, 0 to 10 mol %, 0 to 8 mol %, 0 to 6 mol %, 0 to 4 mol %, >0 to 14 mol %, >0 to 10 mol %, >0 to 8 mol %, >0 to 6 mol %, >0 to 4 mol %, 1 to 14 mol %, 1 to 10 mol %, 1 to 8 mol %, 1 to 6 mol %, 2 to 14 mol %, 2 to 10 mol %, 2 to 8 mol %, 2 to 6 mol %, 4 to 14 mol %, 4 to 10 mol %, 4 to 8 mol %, 6 to 14 mol %, 6 to 10 mol %, 8 to 14 mol % or 8 to 10 mol % $R_2O$. In some embodiments, the glass ceramic and/or the precursor glass can comprise about 0, >0, 1, 2, 3, 4, 5, 6, 7, 8, 9, 10, 11, 12, 13, or 14 mol % $R_2O$.

$Na_2O$ can be useful in the glass ceramic and/or the precursor glass for ion exchange and chemical tempering. In some embodiments, the glass ceramic and/or the precursor glass comprises from 0 mol % to about 5 mol % $Na_2O$ (0 mol %≤$Na_2O$≤5 mol %). In some embodiments, the glass ceramic and/or the precursor glass can comprise from greater than 0 to 5 mol % $Na_2O$. In some embodiments, the glass ceramic and/or the precursor glass can comprise from about 0 to 3 mol % $Na_2O$ or >0 to 3 mol % $Na_2O$. In some embodiments, the glass ceramic and/or the precursor glass can comprise from 0.5 to 4 mol % $Na_2O$. In some embodiments, the glass ceramic and/or the precursor glass can comprise from 0 to 5 mol %, 0 to 4 mol %, 0 to 3 mol %, 0 to 2 mol %, >0 to 5 mol %, >0 to 4 mol %, >0 to 3 mol %, >0 to 2 mol %, 1 to 5 mol %, 1 to 4 mol %, or 1 to 3 mol % $Na_2O$. In some embodiments, the glass ceramic and/or the precursor glass can comprise about 0, >0, 1, 2, 3, 4, or 5 mol % $Na_2O$.

$K_2O$ may also be useful in ion exchange and may be present in the glass ceramic and/or the precursor glass at amounts from 0 mol % to about 10 mol % $K_2O$ (0 mol %≤$K_2O$≤10 mol %). In some embodiments, the glass ceramic and/or the precursor glass can comprise from >0 to 10 mol % $K_2O$. In some embodiments, the glass ceramic and/or the precursor glass can comprise from about 0 to 5 mol % $K_2O$ or >0 to 3 mol % $K_2O$. In some embodiments, the glass ceramic and/or the precursor glass can comprise from 0.5 to 4 mol % $K_2O$. In some embodiments, the glass ceramic and/or the precursor glass can comprise from 0 to 10 mol %, 0 to 8 mol %, 0 to 5 mol %, 0 to 4 mol %, 0 to 3 mol %, >0 to 10 mol %, >0 to 8 mol %, >0 to 5 mol %, >0 to 3 mol %, 1 to 10 mol %, 1 to 8 mol %, 1 to 5, 1 to 4 mol %, 1 to 3 mol %, 2 to 10 mol %, 2 to 8 mol %, or 2 to 4 $K_2O$. In some embodiments, the glass ceramic and/or the precursor glass can comprise about 0, >0, 1, 2, 3, 4, 5, 6, 7, 8, 9, or 10 mol % $K_2O$.

In some embodiments, the precursor glasses and glass ceramics may be Cs and Rb free. In such embodiments, the term $R'_2O$ is used to distinguish from $R_2O$ above, where R' is the sum of the alkali metals Na and K, but does not include Cs, Li, and Rb. In some embodiments, the glass ceramic and/or the precursor glass comprises from 0 mol % to about 14 mol % $R'_2O$ (0 mol %<R'20≤14 mol %). In some embodiments, the glass ceramic and/or the precursor glass can comprise from 0 to 10 mol % or 0 to 8 mol % $R'_2O$. In some embodiments, the glass ceramic and/or the precursor glass can comprise from >0 to 14, >0 to 10, or >0 to 8 mol % $R'_2O$. In some embodiments, the glass ceramic and/or the precursor glass can comprise from 1 to 4 mol % $R'_2O$. In some embodiments, the glass ceramic and/or the precursor glass can comprise from 0 to 14 mol %, 0 to 10 mol %, 0 to 8 mol %, 0 to 6 mol %, 0 to 4 mol %, >0 to 14 mol %, >0 to 10 mol %, >0 to 8 mol %, >0 to 6 mol %, >0 to 4 mol %, 1 to 14 mol %, 1 to 10 mol %, 1 to 8 mol %, 1 to 6 mol %, 2 to 14 mol %, 2 to 10 mol %, 2 to 8 mol %, 2 to 6 mol %, 4 to 14 mol %, 4 to 10 mol %, 4 to 8 mol %, 6 to 14 mol %, 6 to 10 mol %, 8 to 14 mol % or 8 to 10 mol % $R'_2O$. In some embodiments, the glass ceramic and/or the precursor glass can comprise about 0, >0, 1, 2, 3, 4, 5, 6, 7, 8, 9, 10, 11, 12, 13, or 14 mol % $R'_2O$.

Alkaline earth oxides may provide advantages for ion exchange in the glass ceramic or precursor glass, along with improving other properties in the materials. In some embodiments, the glass ceramic and/or the precursor glass comprises from 0 mol % to about 10 mol % MO (0 mol %≤MO≤10 mol %), where M is the sum of the alkaline earth metals Mg, Ca, Sr, and Ba, in the glass ceramic and/or the precursor glass. In some embodiments, the glass ceramic and/or the precursor glass can comprise from 0 to 8 mol % MO. In some embodiments, the glass ceramic and/or the precursor glass can comprise from 0 to 5 mol % MO. In some embodiments, the glass ceramic and/or the precursor glass can comprise from 1 to 8 mol % MO. In some embodiments, the glass ceramic and/or the precursor glass can comprise from 0 to 10 mol %, 0 to 8 mol %, 0 to 6 mol %, 0 to 4 mol %, 1 to 10 mol %, 1 to 8 mol %, 1 to 6 mol % 2 to 10 mol %, 2 to 8 mol %, or 2 to 6 mol % MO. In some embodiments, the glass ceramic and/or the precursor glass can comprise about >0, 1, 2, 3, 4, 5, 6, 7, 8, 9, or 10 mol % MO.

Titanium dioxide, $TiO_2$, can provide improved fracture toughness to the glass ceramic and/or the precursor glass, either alone or in combination with the tetragonal $ZrO_2$. In some embodiments, the glass ceramic and/or the precursor glass may further comprise from 0 mol % to about 10 mol % $TiO_2$, >0 mol % to about 10 mol % $TiO_2$, 0 mol % to about 5 mol % $TiO_2$, or >0 mol % to about 5 mol % $TiO_2$. In some embodiments, the glass ceramic and/or the precursor glass may comprise 0 to 5 mol %, 0 to 4 mol %, 0 to 3 mol %, 0 to 2 mol %, 0 to 1 mol %, >0 to 10 mol %, >0 to 5 mol %, >0 to 4 mol %, >0 to 3 mol %, >0 to 2 mol %, >0 to 1 mol %, 0.01 to 3 mol %, or 0.1 to 2 mol % $TiO_2$.

ZnO may be present in the glass ceramic and/or the precursor glass. In some embodiments, the glass ceramic and/or the precursor glass comprises from 0 mol % to about 5 mol % ZnO (0 mol %≤ZnO≤5 mol %). In some embodiments, the glass ceramic and/or the precursor glass can comprise from greater than 0 to 5 mol % ZnO. In some embodiments, the glass ceramic and/or the precursor glass can comprise from about 0 to 3 mol % ZnO or >0 to 3 mol % ZnO. In some embodiments, the glass ceramic and/or the precursor glass can comprise from 0.5 to 4 mol % ZnO. In some embodiments, the glass ceramic and/or the precursor glass can comprise from 0 to 5 mol %, 0 to 4 mol %, 0 to 3 mol %, 0 to 2 mol %, >0 to 5 mol %, >0 to 4 mol %, >0 to 3 mol %, >0 to 2 mol %, 1 to 5 mol %, 1 to 4 mol %, or 1 to 3 mol % ZnO. In some embodiments, the glass ceramic and/or the precursor glass can comprise about 0, >0, 1, 2, 3, 4, or 5 mol % ZnO.

In some embodiments, the glass ceramics above further comprise a coloring component. The coloring component may comprise, for example, $Fe_2O_3$, $V_2O_5$, $Cr_2O_3$, $TiO_2$, $MnO_2$, NiO, ZnO, CuO, NiO, $Co_3O_4$, rare earth oxides, and combinations thereof. In some cases, the total mol % of coloring component is from 0 to 4 mol %, 0 to 3 mol %, 0 to 2 mol %, 0 to 1 mol %, >0 to 1, >0 to 2, >0 to 3, or >0 to 4 mol %.

Additional components can be incorporated into the glass ceramic and/or the precursor glass to provide additional benefits or may be incorporated as contaminants typically found in commercially-prepared glass. For example, additional components can be added as fining agents (e.g., to facilitate removal of gaseous inclusions from melted batch materials used to produce the glass) and/or for other purposes. In some embodiments, the glass ceramic and/or the precursor glass may comprise one or more compounds useful as ultraviolet radiation absorbers. In some embodiments, the glass ceramic and/or the precursor glass can comprise 3 mol % or less MnO, $Nb_2O_5$, $MoO_3$, $Ta_2O_5$, $WO_3$, $SnO_2$, $Fe_2O_3$, $As_2O_3$, $Sb_2O_3$, Cl, Br, or combinations thereof. In some embodiments, the glass ceramic and/or the precursor glass can comprise from 0 to about 3 mol %, 0 to about 2 mol %, 0 to about 1 mol %, 0 to 0.5 mol %, 0 to 0.1 mol %, 0 to 0.05 mol %, or 0 to 0.01 mol % MnO, ZnO, $Nb_2O_5$, $MoO_3$, $Ta_2O_5$, $WO_3$, $SnO_2$, $Fe_2O_3$, $As_2O_3$, $Sb_2O_3$, Cl, Br, or combinations thereof. In some embodiments, the glass ceramic and/or the precursor glass can comprise from 0 to about 3 mol %, 0 to about 2 mol %, 0 to about 1 mol %, 0 to about 0.5 mol %, 0 to about 0.1 mol %, 0 to about 0.05 mol %, or 0 to about 0.01 mol % $SnO_2$ or $Fe_2O_3$, or combinations thereof. The glasses, according to some embodiments, can also include various contaminants associated with batch materials and/or introduced into the glass by the melting, fining, and/or forming equipment used to produce the glass.

Non-limiting examples of precursor glasses for forming the embodied glass ceramics are listed in Table 1, wherein the values of the components are listed in mol %.

TABLE 1

| | Sample | | | | | | | | | | | | |
|---|---|---|---|---|---|---|---|---|---|---|---|---|---|
| | A | B | C | D | E | F | G | H | I | J | K | L | M |
| $SiO_2$ | 55 | 55 | 55 | 55 | 55 | 55 | 55 | 55 | 55 | 55 | 55 | 55 | 55 |
| $ZrO_2$ | 3 | 3 | 5 | 5 | 10 | 10 | 13 | 15 | 17 | 20 | 20 | 25 | 25 |
| $Li_2O$ | 40 | 25 | 18 | 30 | 20 | 32 | 25 | 20 | 18 | 18 | 20 | 18 | 18 |
| $Na_2O$ | 1 | 5 | 4 | 2 | 1.5 | 2 | 1 | 0.5 | 2 | 4 | 1.5 | 1 | 1 |
| $K_2O$ | 0 | 0 | 1 | 2 | 2.5 | 0 | 4 | 7.5 | 0 | 0.5 | 0 | 0 | 0 |
| MO* | 0 | 4 | 8 | 1 | 7 | 0 | 0.5 | 0 | 1 | 0 | 1 | 0 | 0 |
| $Al_2O_3$ | 0.5 | 2 | 4 | 3 | 0 | 0 | 1 | 0.5 | 0.5 | 0 | 0.5 | 0 | 0.5 |
| $B_2O_3$ | 0 | 1 | 1 | 0.5 | 0 | 0 | 0 | 0 | 0 | 2 | 0 | 0 | 0 |
| $P_2O_5$ | 0.5 | 2 | 1.5 | 0.5 | 4 | 1 | 0.5 | 1 | 2.5 | 0.5 | 1 | 0.75 | 0.5 |
| REO | 0 | 2 | 0.5 | 1 | 0 | 0 | 0 | 0 | 4 | 0 | 0 | 0.25 | 0 |
| Other | 0 | $TiO_2$ 1 | ZnO 2 | 0 | 0 | 0 | 0 | $Cs_2O$ 0.5 | 0 | 0 | $Co_3O_4$ 1 | 0 | 0 |
| | N | O | P | Q | R | S | T | U | V | W | X | Y | Z |
| $SiO_2$ | 60 | 60 | 60 | 60 | 60 | 60 | 58 | 58 | 60 | 60 | 59 | 65 | 65 |
| $ZrO_2$ | 3 | 3 | 5 | 5 | 9 | 10 | 13 | 15 | 17 | 20 | 20 | 3 | 3 |
| $Li_2O$ | 34 | 25 | 18 | 25 | 18 | 27 | 22 | 20 | 18 | 18 | 18 | 18 | 18 |
| $Na_2O$ | 1 | 3 | 4 | 2 | 1.5 | 2 | 1 | 0 | 0 | 1 | 1.25 | 1 | 5 |
| $K_2O$ | 0 | 0 | 3 | 2 | 0.5 | 0 | 3 | 5 | 0 | 0.4 | 0 | 7 | 0 |
| MO* | 1 | 2 | 8 | 1 | 7 | 0 | 0.5 | 0 | 0 | 0 | 0 | 1.5 | 0 |
| $Al_2O_3$ | 0.5 | 2 | 0 | 3 | 0 | 0 | 0 | 0.5 | 0.5 | 0 | 0.25 | 0 | 5 |
| $B_2O_3$ | 0 | 1 | 0 | 0.5 | 0 | 0 | 0 | 0 | 0 | 0.5 | 0 | 0 | 0 |
| $P_2O_5$ | 0.5 | 2 | 1.5 | 0.5 | 4 | 1 | 0.5 | 1.5 | 0.5 | 0.1 | 1 | 4 | 3 |
| REO | 0 | 2 | 0.5 | 1 | 0 | 0 | 0 | 0 | 4 | 0 | 0 | 0.5 | 1 |
| Other | 0 | 0 | 0 | 0 | 0 | 0 | $TiO_2$ 2 | 0 | 0 | 0 | $Rb_2O$ 0.5 | 0 | 0 |
| | AA | AB | AC | AD | AE | AF | AG | AH | AI | AJ | AK | AL | AM |
| $SiO_2$ | 65 | 65 | 64 | 65 | 64 | 65 | 65 | 70 | 69 | 70 | 70 | 70 | 70 |
| $ZrO_2$ | 3 | 5 | 5 | 9 | 10 | 13 | 15 | 3 | 3 | 3 | 5 | 5 | 9 |
| $Li_2O$ | 30 | 20 | 24 | 18 | 24 | 20 | 18 | 20 | 18 | 20 | 20 | 23 | 20 |
| $Na_2O$ | 1 | 4 | 0.5 | 3 | 1 | 0.3 | 0.7 | 2 | 2 | 1.5 | 2.5 | 1.5 | 0.5 |
| $K_2O$ | 0 | 1 | 1.8 | 0.5 | 0 | 0.2 | 0.3 | 1 | 0 | 0 | 0 | 0 | 0 |
| MO* | 0 | 1 | 0 | 0.5 | 0 | 1 | 0 | 0.5 | 5 | 2 | 0.7 | 0 | 0 |
| $Al_2O_3$ | 0.5 | 2 | 1 | 2 | 0 | 0 | 0.3 | 1 | 1 | 1 | 0 | 0 | 0 |
| $B_2O_3$ | 0 | 0 | 0.6 | 0 | 0 | 0 | 0 | 0.5 | 0 | 0 | 1 | 0 | 0 |
| $P_2O_5$ | 0.5 | 1.8 | 3 | 1 | 1 | 0.5 | 0.5 | 2 | 1 | 2.5 | 1.5 | 1 | 0.5 |
| REO | 0 | 0.2 | 0.1 | 0 | 0 | 0 | 0.2 | 0 | 0 | 0 | 0.3 | 0 | 0 |

*MO = CaO + MgO + SrO + BaO

As noted above, the glass ceramic described herein comprise a tetragonal $ZrO_2$ crystalline phase and a lithium disilicate phase. In some embodiments, the glass ceramics described herein may also contain other secondary crystalline phases. Such phases may be beneficial for toughening or for chemical strengthening by ion exchange processes known in the art (as is the case for β-spodumene solid solutions or glass). In some cases, the crystalline phases are interlocked or the crystals are very close together, leaving an intermixed glass phase. These unique microstructures and phase assemblages are not available using traditional ceramic processing routes—the disclosed method gives these microstructures by homogenous nucleation of the precursor glass that results in the disclosed phase assemblages and microstructures without the use of high temperature sintering or the hazard of inhomogeneous dispersion of a $ZrO_2$ phase in molten glass. Additionally, certain phases may also serve to decrease the coefficient of thermal expansion (CTE) of the glass ceramic material. Accordingly, the glass ceramic may further comprise at least one of a lithium aluminosilicate phase, a cristobalite phase, a β-spodumene phase, a lithiophosphate ($Li_3PO_4$) crystalline phase, a crystalline lithium orthophosphate phase, a quartz solid solution phase, a baddeleyite phase, a lithium metasilicate ($Li_2SiO_3$) phase, a monoclinic zirconia phase, a zekzerite phase, a cubic zirconia phase, or a crystalline $(Na,Li)ZrSi_6O_{18}$ phase. As used herein the term "quartz solid solution" includes solid solutions of $SiO_2$ and up to about 50 wt % $Li(AlO_2)$.

Non-limiting examples of embodied ranges for glass ceramics are listed in Table 2, wherein the values of the components are listed in mol %.

| Sample | I | II | III | IV |
|---|---|---|---|---|
| $SiO_2$ | 50-80 | 55-70 | 58-69 | 50-80 |
| $Al_2O_3$ | 0-5 | 0-5 | 0-5 | 0-5 |
| $B_2O_3$ | 0-5 | 0-5 | 0-5 | 0-5 |
| $Li_2O$ | 18-40 | 18-40 | 18-40 | 18-30 |
| $Na_2O$ | 0-5 | 0-5 | 0-5 | 0-5 |
| MO | 0-10 | 0-10 | 0-10 | 0-10 |
| ZnO | 0-5 | 0-5 | 0-5 | 0-5 |
| $ZrO_2$ | 1.5-25 | 1.5-25 | 1.5-25 | 1.5-25 |
| $P_2O_5$ | >0-5 | >0-5 | >0-5 | >0-5 |
| REO | 0-5 | 0-5 | 0-5 | 0-5 |
| Ceramming cycle | One of C1-C4 | | | |
| Phase assemblage | t-$ZrO_2$, lithium disilicate, plus minor phases including m-$ZrO_2$, cristobalite, lithiophosphate, zektzerite | | | |

| Sample | V | VI | VII | VIII |
|---|---|---|---|---|
| $SiO_2$ | 55-70 | 58-69 | 50-80 | 55-70 |
| $Al_2O_3$ | 0-5 | 0-5 | 0-5 | 0-5 |
| $B_2O_3$ | 0-5 | 0-5 | 0-5 | 0-5 |
| $Li_2O$ | 18-30 | 18-30 | 25-36 | 25-36 |
| $Na_2O$ | 0-5 | 0-5 | 0-5 | 0-5 |
| MO | 0-10 | 0-10 | 0-10 | 0-10 |
| ZnO | 0-5 | 0-5 | 0-5 | 0-5 |
| $ZrO_2$ | 1.5-25 | 1.5-25 | 1.5-25 | 1.5-25 |
| $P_2O_5$ | >0-5 | >0-5 | >0-5 | >0-5 |
| REO | 0-5 | 0-5 | 0-5 | 0-5 |
| Ceramming cycle | One of C1-C4 | | | |
| Phase assemblage | t-$ZrO_2$, lithium disilicate, plus minor phases including m-$ZrO_2$, cristobalite, lithiophosphate, zektzerite | | | |

| Sample | IX | X | XI | XII |
|---|---|---|---|---|
| $SiO_2$ | 58-69 | 55-70 | 58-69 | 55-70 |
| $Al_2O_3$ | 0-5 | 0-5 | 0-5 | 0-5 |
| $B_2O_3$ | 0-5 | 0-5 | 0-5 | 0-5 |
| $Li_2O$ | 25-36 | 18-40 | 18-40 | 18-40 |
| $Na_2O$ | 0-5 | 0-5 | 0-5 | 0-5 |
| MO | 0-10 | 0-10 | 0-10 | 0-10 |
| ZnO | 0-5 | 0-5 | 0-5 | 0-5 |
| $ZrO_2$ | 1.5-25 | 4-20 | 4-20 | 6-15 |
| $P_2O_5$ | >0-5 | >0-5 | >0-5 | >0-5 |
| REO | 0-5 | 0-5 | 0-5 | 0-5 |
| Ceramming cycle | One of C1-C4 | | | |
| Phase assemblage | t-$ZrO_2$, lithium disilicate, plus minor phases including m-$ZrO_2$, cristobalite, lithiophosphate, zektzerite | | | |

| Sample | XIII | XIV | XV | XVI |
|---|---|---|---|---|
| $SiO_2$ | 58-69 | 55-70 | 58-69 | 50-80 |
| $Al_2O_3$ | 0-5 | 0-5 | 0-5 | 0-5 |
| $B_2O_3$ | 0-5 | 0-5 | 0-5 | 0-5 |
| $Li_2O$ | 18-40 | 18-40 | 18-40 | 18-30 |
| $Na_2O$ | 0-5 | 0-5 | 0-5 | 0-5 |
| MO | 0-10 | 0-10 | 0-10 | 0-10 |
| ZnO | 0-5 | 0-5 | 0-5 | 0-5 |
| $ZrO_2$ | 6-15 | 1.5-25 | 1.5-25 | 4-20 |
| $P_2O_5$ | >0-5 | 0.2-5 | 0.2-5 | >0-5 |
| REO | 0-5 | 0-5 | 0-5 | 0-5 |

-continued

| Ceramming cycle | One of C1-C4 | | | |
|---|---|---|---|---|
| Phase assemblage | t-$ZrO_2$, lithium disilicate, plus minor phases including m-$ZrO_2$, cristobalite, lithiophosphate | | | |
| Sample | XVII | XVIII | XIX | XX |
| $SiO_2$ | 50-80 | 50-80 | 50-80 | 55-70 |
| $Al_2O_3$ | 0-5 | 0-5 | 0-5 | 0-5 |
| $B_2O_3$ | 0-5 | 0-5 | 0-5 | 0-5 |
| $Li_2O$ | 25-36 | 18-30 | 25-36 | 18-30 |
| $Na_2O$ | 0-5 | 0-5 | 0-5 | 0-5 |
| MO | 0-10 | 0-10 | 0-10 | 0-10 |
| ZnO | 0-5 | 0-5 | 0-5 | 0-5 |
| $ZrO_2$ | 4-20 | 6-15 | 6-15 | 4-20 |
| $P_2O_5$ | >0-5 | >0-5 | >0-5 | >0-5 |
| REO | 0-5 | 0-5 | 0-5 | 0-5 |
| Ceramming cycle | One of C1-C4 | | | |
| Phase assemblage | t-$ZrO_2$, lithium disilicate, plus minor phases including m-$ZrO_2$, cristobalite, lithiophosphate, zektzerite | | | |
| Sample | XXI | XXII | XXIII | XIV |
| $SiO_2$ | 55-70 | 58-69 | 58-69 | 58-69 |
| $Al_2O_3$ | 0-5 | 0-5 | 0-5 | 0-5 |
| $B_2O_3$ | 0-5 | 0-5 | 0-5 | 0-5 |
| $Li_2O$ | 25-36 | 18-30 | 25-36 | 18-30 |
| $Na_2O$ | 0-5 | 0-5 | 0-5 | 0-5 |
| MO | 0-10 | 0-10 | 0-10 | 0-10 |
| ZnO | 0-5 | 0-5 | 0-5 | 0-5 |
| $ZrO_2$ | 6-15 | 4-20 | 6-15 | 6-15 |
| $P_2O_5$ | >0-5 | >0-5 | >0-5 | 0.2-5 |
| REO | 0-5 | 0-5 | 0-5 | 0-5 |
| Ceramming cycle | One of C1-C4 | | | |
| Phase assemblage | t-$ZrO_2$, lithium disilicate, plus minor phases including m-$ZrO_2$, cristobalite, lithiophosphate, zektzerite | | | |

C1: 2 hr at 700° C., 4 hr at 850° C. (±1 hour, ±25° C. for each)
C2: 2 hr at 700° C., 4 hr at 875° C. (±1 hour, ±25° C. for each)
C3: 2 hr at 750° C., 4 hr at 900° C. (±1 hour, ±25° C. for each)
C4: 2 hr at 800° C., 4 hr at 900° C. (±1 hour, ±25° C. for each)

In addition to having high fracture toughness, the glass ceramics described herein can have color and transparency/translucency properties that make them advantageous for a number of applications. The glass ceramics of one or more embodiments may exhibit a substantially white, "pearl," milky, or white-translucent color. In some embodiments, the glass ceramics exhibit a color presented in CIELAB color space coordinates (determined from reflectance spectra measurements using a spectrophotometer, with illuminant D65 and specular reflectance excluded), of the following ranges: a*=from about −1 to about +3; b*=from about −7 to about +3; and L*>85. In some applications, the glass ceramics are translucent and quantitatively white to yellow-brown in color and are of particular interest in dental applications. In such applications, it may be desirable to have glass ceramics with CIELAB color space coordinates: a*=from about −1 to about 1; b*=from about −4 to about 1; and L*<60. In some embodiments, the glass ceramics are qualitatively described as white and opaque and have a color presented in CIELAB color space coordinates: a*=from about −1 to about 0; b*=from about −2 to about 0; and L*>88. In some embodiments, the glass ceramics are qualitatively described as black and opaque and have a color presented in CIELAB color space coordinates: a*=from about −1 to about 1; b*=from about −1 to about 1; and L*<40.

Non-limiting examples of precursor glasses and glass ceramic compositions, heat treatment (ceramming) schedules, and phase assemblages resulting from different ceramming/heat treatment schedules are listed in Table 3. Table 3 also includes comments regarding the general appearance of the formed glass ceramic.

Table 3. Examples of precursor compositions (expressed in mol %), ceramming schedules, and phase assemblages resulting from different heat treatment schedules. Note: in Table 3 tetragonal $ZrO_2$ is denoted by "t-$ZrO_2$," monoclinic $ZrO_2$ is denoted by "m-$ZrO_2$," and quartz solid solution is denoted by "quartz S.S."

| Example | 1 | 2 | 3 | 4 |
|---|---|---|---|---|
| $SiO_2$ | 67.0 | 63.9 | 61.1 | 58.5 |
| $Al_2O_3$ | 0 | 0 | 0 | 0 |
| $Li_2O$ | 27.2 | 25.9 | 24.8 | 23.7 |
| $Na_2O$ | 1.5 | 1.4 | 1.3 | 1.3 |
| MgO | 0 | 0 | 0 | 0 |
| ZnO | 0 | 0 | 0 | 0 |
| CaO | 0 | 0 | 0 | 0 |
| $ZrO_2$ | 2.9 | 7.4 | 11.5 | 15.3 |
| $P_2O_5$ | 1.5 | 1.4 | 1.3 | 1.3 |
| $Y_2O_3$ | 0 | 0 | 0 | 0 |

-continued

| | | | | |
|---|---|---|---|---|
| $SnO_2$ | 0 | 0 | 0 | 0 |
| Ceramming cycle | 2 hr at 750° C., 4 hr at 900° C. | 2 hr at 750° C., 4 hr at 900° C. | 2 hr at 800° C., 4 hr at 900° C. | 2 hr at 700° C., 4 hr at 850° C. |
| Phase assemblage | lithium disilicate, cristobalite, lithiophosphate | lithium disilicate, quartz, cristobalite, lithiophosphate | t-$ZrO_2$, lithium disilicate, cristobalite, baddeleyite, lithiophosphate | glass |
| Appearance | Translucent white | Translucent white | Opaque white | Transparent |
| Fracture toughness (MPa · $m^{1/2}$) | 3.88 | 5.25 | 6.13 | |

| Example | 5 | 6 | 7 | 8 |
|---|---|---|---|---|
| $SiO_2$ | 57.3 | 54.1 | 57.3 | 56.2 |
| $Al_2O_3$ | 0 | 0 | 0 | 0 |
| $Li_2O$ | 34.0 | 32.1 | 34.0 | 33.3 |
| $Na_2O$ | 1.5 | 1.4 | 1.5 | 1.4 |
| MgO | 0 | 0 | 0 | 0 |
| ZnO | 0 | 0 | 0 | 0 |
| CaO | 0 | 0 | 0 | 0 |
| $ZrO_2$ | 5.8 | 11.0 | 5.8 | 7.6 |
| $P_2O_5$ | 1.5 | 1.4 | 1.5 | 1.4 |
| $Y_2O_3$ | 0 | 0 | 0 | 0 |
| $SnO_2$ | 0 | 0 | 0 | 0 |
| Ceramming cycle | 2 hr at 700° C., 4 hr at 850° | 2 hr at 700° C., 4 hr at 850° C. | 2 hr at 750° C., 4 hr at 850° C. | 2 hr at 700° C., 4 hr at 875° C. |
| Phase assemblage | t-$ZrO_2$, lithium disilicate, lithium metasilicate, baddeleyite, lithiophosphate | t-$ZrO_2$, lithium metasilicate, cristobalite, baddeleyite, lithiophosphate | t-$ZrO_2$, lithium disilicate, lithium metasilicate, baddeleyite, lithiophosphate | t-$ZrO_2$, lithium disilicate, lithium metasilicate, baddeleyite, lithiophosphate |
| Appearance | Opaque white | Opaque white | Opaque white | Opaque white |
| Fracture toughness (MPa · $m^{1/2}$) | 2.73 | 2.36 | 3.00 | 3.8 |
| Flexural strength (MPa) | | | 556 | 500 |
| Ceramming cycles | 2 hr at 700° C., 4 hr at 850° C. | 2 hr at 700° C., 4 hr at 850° C. | 2 hr at 750° C., 4 hr at 900° C. | 2 hr at 750° C., 4 hr at 900° C. |
| Fracture toughness (MPa · $m^{1/2}$) | | | 3.90 | 5.30 |

| Example | 9 | 10 | 11 | 12 |
|---|---|---|---|---|
| $SiO_2$ | 55.1 | 54.1 | 62.1 | 59.3 |
| $Al_2O_3$ | 0 | 0 | 0 | 0 |
| $Li_2O$ | 32.7 | 32.1 | 30.1 | 28.7 |
| $Na_2O$ | 1.4 | 1.4 | 1.5 | 1.4 |
| MgO | 0 | 0 | 0 | 0 |
| ZnO | 0 | 0 | 0 | 0 |
| CaO | 0 | 0 | 0 | 0 |
| $ZrO_2$ | 9.3 | 11.0 | 4.9 | 9.3 |
| $P_2O_5$ | 1.4 | 1.4 | 1.5 | 1.4 |
| $Y_2O_3$ | 0 | 0 | 0 | 0 |
| $SnO_2$ | 0 | 0 | 0 | 0 |
| Ceramming cycle | 2 hr at 700° C., 4 hr at 850° C. | 2 hr at 700° C., 4 hr at 850° C. | 2 hr at 700° C., 4 hr at 850° C. | 2 hr at 700° C., 4 hr at 850° C. |
| Phase assemblage | t-$ZrO_2$, lithium disilicate, lithium metasilicate, baddeleyite, lithiophosphate | t-$ZrO_2$, lithium disilicate, lithium metasilicate, baddeleyite, lithiophosphate | t-$ZrO_2$, lithium disilicate, Baddeleyite, lithiophosphate | t-$ZrO_2$, lithium disilicate, lithium metasilicate, baddeleyite, cristobalite, lithiophosphate |
| Appearance | Opaque white | Opaque white | Opaque white | Opaque white |
| Fracture toughness (MPa · $m^{1/2}$) | 3.77 | | 2.28 | 3.15 |
| Flexural strength (MPa) | 191 | | | |
| Ceramming cycles | 2 hr at 750° C., 6 hr at 900° C. | 2 hr at 750° C., 4 hr at 900° C. | 2 hr at 700° C., 4 hr at 850° C. | 2 hr at 700° C., 4 hr at 850° C. |
| Fracture toughness (MPa · $m^{1/2}$) | 7.93 | 6.10 | | |

| Example | 13 | 14 | 15 | 16 |
|---|---|---|---|---|
| $SiO_2$ | 59.5 | 60.3 | 63.5 | 64.9 |
| $Al_2O_3$ | 0 | 0 | 0 | 0 |
| $Li_2O$ | 29.7 | 30.3 | 27.8 | 26.7 |
| $Na_2O$ | 1.4 | 1.3 | 1.2 | 1.2 |

-continued

| | | | | |
|---|---|---|---|---|
| MgO | 0 | 0 | 0 | 0 |
| ZnO | 0 | 0 | 0 | 0 |
| CaO | 0 | 0 | 0 | 0 |
| $ZrO_2$ | 7.7 | 6.9 | 6.3 | 6.1 |
| $P_2O_5$ | 1.4 | 1.3 | 1.2 | 1.1 |
| $Y_2O_3$ | 0.2 | 0 | 0 | 0 |
| $SnO_2$ | | 0 | 0 | 0 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, m-$ZrO_2$, lithium disilicate quartz s.s., $SiO_2$, lithiophosphate | t-$ZrO_2$, m-$ZrO_2$, lithium disilicate $SiO_2$, lithiophosphate | t-$ZrO_2$, m-$ZrO_2$, lithium disilicate $SiO_2$, cristobalite lithiophosphate, lithium metasilicate, $NaLiZrSi_6O_{18}$ | t-$ZrO_2$, $SiO_2$, $ZrSiO_4$, lithium disilicate cristobalite lithiophosphate, lithium metasilicate, $NaLiZrSi_6O_{18}$ |
| Appearance | white opaque, medium grained | white, opaque, fine grained | layered, broken up on ceramming | layered, broken up on ceramming |

| Example | 17 | 18 | 19 | 20 |
|---|---|---|---|---|
| $SiO_2$ | 66.2 | 67.4 | 68.5 | 69.5 |
| $Al_2O_3$ | 0 | 0 | 0 | 0 |
| $Li_2O$ | 25.7 | 24.8 | 24 | 23.2 |
| $Na_2O$ | 1.1 | 1.1 | 1 | 1 |
| MgO | 0 | 0 | 0 | 0 |
| ZnO | 0 | 0 | 0 | 0 |
| CaO | 0 | 0 | 0 | 0 |
| $ZrO_2$ | 5.9 | 5.7 | 5.5 | 5.3 |
| $P_2O_5$ | 1.1 | 1.1 | 1 | 1 |
| $Y_2O_3$ | 0 | 0 | 0 | 0 |
| $SnO_2$ | 0 | 0 | 0 | 0 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, m-$ZrO_2$, lithium disilicate cristobalite lithiophosphate | t-$ZrO_2$, m-$ZrO_2$, lithium disilicate cristobalite lithiophosphate | t-$ZrO_2$, m-$ZrO_2$, lithium disilicate cristobalite lithiophosphate | t-$ZrO_2$, m-$ZrO_2$, lithium disilicate cristobalite lithiophosphate zektzerite |
| Appearance | white, opaque, fine grained | white opaque, fine to medium grain | white opaque, fine to medium grain | broke up on ceramming, flaky |

| Example | 21 | 22 | 23 | 24 |
|---|---|---|---|---|
| $SiO_2$ | 70.5 | 71.4 | 72.3 | 62.1 |
| $Al_2O_3$ | 0 | 0 | 0 | 0 |
| $Li_2O$ | 22.4 | 21.7 | 21.1 | 29.7 |
| $Na_2O$ | 1 | 0.9 | 0.9 | 1.3 |
| MgO | 0 | 0 | 0.0 | 0 |
| ZnO | 0 | 0 | 0 | 0 |
| CaO | 0 | 0 | 0 | 0 |
| $ZrO_2$ | 5.1 | 5 | 4.8 | 5.6 |
| $P_2O_5$ | 1 | 0.9 | 0.9 | 1.4 |
| $Y_2O_3$ | 0 | 0 | 0 | 0 |
| $SnO_2$ | 0 | 0 | 0 | 0 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, m-$ZrO_2$, lithium disilicate cristobalite lithiophosphate zektzerite | t-$ZrO_2$, m-$ZrO_2$, lithium disilicate cristobalite lithiophosphate zektzerite | t-$ZrO_2$, m-$ZrO_2$, lithium disilicate cristobalite lithiophosphate zektzerite | t-$ZrO_2$, m-$ZrO_2$, lithium disilicate cristobalite lithiophosphate |
| Appearance | white opaque, fine to medium grain | white opaque, fine to medium grain | white opaque | white opaque |

| Example | 25 | 26 | 27 | 28 |
|---|---|---|---|---|
| $SiO_2$ | 71.4 | 72.3 | 62.1 | 63.4 |
| $Al_2O_3$ | 0 | 0 | 0 | 0 |
| $Li_2O$ | 21.7 | 21.1 | 29.7 | 29.4 |
| $Na_2O$ | 0.9 | 0.9 | 1.3 | 1.3 |
| MgO | 0 | 0 | 0 | 0 |
| ZnO | 0 | 0 | 0 | 0 |
| CaO | 0 | 0 | 0 | 0 |
| $ZrO_2$ | 5 | 4.8 | 5.6 | 4.6 |
| $P_2O_5$ | 0.9 | 0.9 | 1.4 | 1.3 |
| $Y_2O_3$ | 0 | 0 | 0 | 0 |
| $SnO_2$ | 0 | 0 | 0 | 0 |

-continued

| | | | | |
|---|---|---|---|---|
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, m-$ZrO_2$, lithium disilicate cristobalite lithiophosphate | t-$ZrO_2$, m-$ZrO_2$, lithium disilicate cristobalite lithiophosphate | lithium disilicate cristobalite lithiophosphate | t-$ZrO_2$, m-$ZrO_2$, lithium disilicate cristobalite lithiophosphate |
| Appearance | white opaque | white opaque | white translucent | |

| Example | 29 | 30 | 31 | 32 |
|---|---|---|---|---|
| $SiO_2$ | 64.6 | 65.8 | 68.4 | 69.7 |
| $Al_2O_3$ | 0 | 0 | 0 | 0 |
| $Li_2O$ | 29.1 | 28.8 | 24.0 | 23.7 |
| $Na_2O$ | 1.3 | 1.3 | 1.1 | 1.1 |
| MgO | 0 | 0 | 0 | 0 |
| ZnO | 0 | 0 | 0 | 0 |
| CaO | 0 | 0 | 0 | 0 |
| $ZrO_2$ | 3.7 | 2.8 | 5.5 | 4.5 |
| $P_2O_5$ | 1.3 | 1.3 | 1.0 | 1.0 |
| $Y_2O_3$ | 0 | 0 | 0 | 0 |
| $SnO_2$ | 0 | 0 | 0 | 0 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, m-$ZrO_2$, lithium disilicate cristobalite lithiophosphate | t-$ZrO_2$, m-$ZrO_2$, lithium disilicate cristobalite lithiophosphate | t-$ZrO_2$, lithium disilicate cristobalite lithiophosphate | t-$ZrO_2$, m-$ZrO_2$, lithium disilicate cristobalite lithiophosphate |
| Appearance | | | | |

| Example | 33 | 34 | 35 | 36 |
|---|---|---|---|---|
| $SiO_2$ | 70.9 | 70.1 | 70 | 70 |
| $Al_2O_3$ | 0 | 0.5 | 0.8 | 1 |
| $Li_2O$ | 23.5 | 23.2 | 23.2 | 23.2 |
| $Na_2O$ | 1.1 | 0.9 | 0.9 | 0.9 |
| MgO | 0 | 0 | 0 | 0 |
| ZnO | 0 | 0 | 0 | 0 |
| CaO | 0 | 0 | 0 | 0 |
| $ZrO_2$ | 3.5 | 4.3 | 4.1 | 3.8 |
| $P_2O_5$ | 1 | 1 | 1 | 1 |
| $Y_2O_3$ | 0 | 0 | 0 | 0 |
| $SnO_2$ | 0 | 0 | 0 | 0 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, m-$ZrO_2$, lithium disilicate cristobalite lithiophosphate | t-$ZrO_2$, α-quartz m-$ZrO_2$, lithium disilicate cristobalite lithiophosphate | t-$ZrO_2$, α-quartz m-$ZrO_2$, lithium disilicate cristobalite lithiophosphate | t-$ZrO_2$, α-quartz m-$ZrO_2$, lithium disilicate cristobalite lithiophosphate |
| Appearance | | | | |

| Example | 37 | 38 | 39 | 40 |
|---|---|---|---|---|
| $SiO_2$ | 70.3 | 70.1 | 69.9 | 69.6 |
| $Al_2O_3$ | 1 | 1.3 | 1.6 | 1.35 |
| $Li_2O$ | 23.3 | 23.2 | 23.2 | 23.4 |
| $Na_2O$ | 0 | 0 | 0 | 0.94 |
| MgO | 0 | 0 | 0 | 0 |
| ZnO | 0 | 0 | 0 | 0 |
| CaO | 0 | 0 | 0 | 0 |
| $ZrO_2$ | 4.3 | 4.3 | 4.3 | 3.58 |
| $P_2O_5$ | 1 | 1 | 1 | 1 |
| $Y_2O_3$ | 0 | 0 | 0 | 0 |
| $SnO_2$ | 0 | 0 | 0 | 0.08 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, α-quartz m-$ZrO_2$, lithium disilicate cristobalite lithiophosphate | t-$ZrO_2$, α-quartz m-$ZrO_2$, lithium disilicate cristobalite lithiophosphate | t-$ZrO_2$, α-quartz m-$ZrO_2$, lithium disilicate cristobalite lithiophosphate | t-$ZrO_2$, α-quartz m-$ZrO_2$, lithium disilicate cristobalite lithiophosphate |
| Appearance | | | | |

| Example | 41 | 42 | 43 | 44 |
|---|---|---|---|---|
| $SiO_2$ | 69.6 | 69.72 | 70.59 | 70.65 |
| $Al_2O_3$ | 1.45 | 2.67 | 3.81 | 4.27 |

-continued

| | | | | |
|---|---|---|---|---|
| $Li_2O$ | 23.42 | 23.33 | 22.22 | 22.06 |
| $Na_2O$ | 0.9 | 0.45 | 0.17 | 0.06 |
| MgO | 0 | 0 | 0 | 0 |
| ZnO | 0 | 0 | 0 | 0 |
| CaO | 0 | 0 | 0 | 0 |
| $ZrO_2$ | 3.53 | 2.81 | 2.22 | 1.97 |
| $P_2O_5$ | 1.0 | 0.91 | 0.86 | 0.85 |
| $Y_2O_3$ | 0 | 0 | 0 | 0 |
| $SnO_2$ | 0.08 | 0.08 | 0.08 | 0.08 |
| Ceramming cycle | 2 hr at 700° C., 4 hr at 875° C. | 2 hr at 700° C., 4 hr at 875° C. | 2 hr at 700° C., 4 hr at 875° C. | 2 hr at 700° C., 4 hr at 875° C. |
| Phase assemblage | t-$ZrO_2$, α-quartz β-spodumene m-$ZrO_2$, lithium disilicate cristobalite lithiophosphate | t-$ZrO_2$, α-quartz β-spodumene m-$ZrO_2$, lithium disilicate cristobalite lithiophosphate | β-spodumene t-$ZrO_2$, α-quartz m-$ZrO_2$, lithium disilicate cristobalite lithiophosphate | β-spodumene t-$ZrO_2$, α-quartz m-$ZrO_2$, lithium disilicate cristobalite lithiophosphate |
| Appearance | | | | |

| Example | 45 | 46 | 47 | 48 |
|---|---|---|---|---|
| $SiO_2$ | 68.6 | 64.1 | 56.2 | 56.2 |
| $Al_2O_3$ | 1.3 | 0.0 | 0 | 0 |
| $Li_2O$ | 22.7 | 22.4 | 29.5 | 32 |
| $Na_2O$ | 0.9 | 1.0 | 1.4 | 1.4 |
| MgO | 1.0 | 0.0 | 0 | 0 |
| ZnO | 1.0 | 0.0 | 0 | 0 |
| CaO | 0 | 6.4 | 3.8 | 0 |
| $ZrO_2$ | 3.5 | 5.1 | 7.6 | 7.6 |
| $P_2O_5$ | 1.0 | 1.0 | 1.4 | 1.4 |
| $Y_2O_3$ | 0 | 0 | 0 | 0.9 |
| $SnO_2$ | 0 | 0 | 0 | 0 |
| Ceramming cycle | 2 hr at 700° C., 4 hr at 875° C. | 2 hr at 700° C., 4 hr at 875° C. | | |
| Phase assemblage | t-$ZrO_2$, α-quartz m-$ZrO_2$, lithium disilicate lithiophosphate | m-$ZrO_2$, lithium disilicate lithiophosphate lithium metasilicate zektzerite | | |
| Appearance | | | | |

| Example | 49 | 50 | 51 | 52 |
|---|---|---|---|---|
| $SiO_2$ | 60.3 | 61.3 | 60.3 | 61.3 |
| $B_2O_3$ | 0 | 1 | 2 | 2 |
| $Li_2O$ | 30.3 | 30.3 | 30.3 | 30.3 |
| $Na_2O$ | 1.3 | 1.3 | 1.3 | 1.3 |
| MgO | 0 | 0 | 0 | 0 |
| ZnO | 0 | 0 | 0 | 0 |
| CaO | 0 | 0 | 0 | 0 |
| $ZrO_2$ | 6.9 | 4.9 | 4.9 | 3.9 |
| $P_2O_5$ | 1.3 | 1.3 | 1.3 | 1.3 |
| $Y_2O_3$ | 0 | 0 | 0 | 0 |
| $SnO_2$ | 0 | 0 | 0 | 0 |
| Phase assemblage | t-$ZrO_2$, lithium disilicate | t-$ZrO_2$, lithium disilicate | t-$ZrO_2$, lithium disilicate | t-$ZrO_2$, lithium disilicate |
| Ceramming cycle | 2 hr at 750° C., 4 hr at 850° C. | 2 hr at 750° C., 4 hr at 850° C. | 2 hr at 750° C., 4 hr at 850° C. | 2 hr at 750° C., 4 hr at 850° C. |
| Appearance | | Smooth, semi glassy white | Course white | Smooth, fine, glassy white |
| Ceramming cycle | 2 hr at 750° C., 4 hr at 875° C. | 2 hr at 750° C., 4 hr at 875° C. | 2 hr at 750° C., 4 hr at 875° C. | 2 hr at 750° C., 4 hr at 875° C. |
| Appearance | | Less glassy than 850 | Course white | Smooth, fine, glassy white |
| Ceramming cycle | 2 hr at 750° C., 4 hr at 900° C. | 2 hr at 750° C., 4 hr at 900° C. | 2 hr at 750° C., 4 hr at 900° C. | 2 hr at 750° C., 4 hr at 900° C. |
| Appearance | | Less glassy than 850 | Course white | Smooth, fine, glassy white |

| Example | 53 | 54 | 55 | 56 |
|---|---|---|---|---|
| $SiO_2$ | 62.3 | 60.3 | 61.3 | 62.3 |
| $B_2O_3$ | 1 | 1.3 | 2.3 | 2 |
| $Li_2O$ | 30.3 | 30.3 | 30.3 | 30.3 |
| $Na_2O$ | 1.3 | 0 | 0 | 1.3 |
| MgO | 0 | 0 | 0 | 0 |
| ZnO | 0 | 0 | 0 | 0 |
| CaO | 0 | 0 | 0 | 0 |

-continued

| | | | | |
|---|---|---|---|---|
| $ZrO_2$ | 3.9 | 6.9 | 4.9 | 2.9 |
| $P_2O_5$ | 1.3 | 1.3 | 1.3 | 1.3 |
| $Y_2O_3$ | 0 | 0 | 0 | 0 |
| $SnO_2$ | 0 | 0 | 0 | 0 |
| Phase assemblage | t-$ZrO_2$, lithium disilicate | t-$ZrO_2$, lithium disilicate | t-$ZrO_2$, lithium disilicate | lithium disilicate |
| Ceramming cycle | 2 hr at 750° C., 4 hr at 850° C. | 2 hr at 750° C., 4 hr at 850° C. | 2 hr at 750° C., 4 hr at 850° C. | 2 hr at 750° C., 4 hr at 850° C. |
| Appearance | Smooth, courser than #52 | Fine, less glassy than #50 | Fine, less glassy than #50 | Glassy, translucent |
| Ceramming cycle | 2 hr at 750° C., 4 hr at 875° C. | 2 hr at 750° C., 4 hr at 875° C. | 2 hr at 750° C., 4 hr at 875° C. | 2 hr at 750° C., 4 hr at 875° C. |
| Appearance | Smooth, higher coarseness than 850 | Fine, less glassy than #50 | Fine, slightly more course than #54 | Glassy, translucent |
| Ceramming cycle | 2 hr at 750° C., 4 hr at 900° C. | 2 hr at 750° C., 4 hr at 900° C. | 2 hr at 750° C., 4 hr at 900° C. | 2 hr at 750° C., 4 hr at 900° C. |
| Appearance | Smooth, higher coarseness than 875 | Medium grain | Fine, slightly more course than #54 | Glassy, translucent |

| Example | 57 | 58 |
|---|---|---|
| $SiO_2$ | 61.3 | 63.3 |
| $B_2O_3$ | 3 | 1 |
| $Li_2O$ | 30.3 | 30.3 |
| $Na_2O$ | 1.3 | 1.3 |
| MgO | 0 | 0 |
| ZnO | 0 | 0 |
| CaO | 0 | 0 |
| $ZrO_2$ | 2.9 | 2.9 |
| $P_2O_5$ | 1.3 | 1.3 |
| $Y_2O_3$ | 0 | 0 |
| $SnO_2$ | 0 | 0 |
| Phase assemblage | lithium disilicate | lithium disilicate |
| Ceramming cycle | 2 hr at 750° C., 4 hr at 850° C. | 2 hr at 750° C., 4 hr at 850° C. |
| Appearance | Glassy, translucent | Glassy, translucent |
| Ceramming cycle | 2 hr at 750° C., 4 hr at 875° C. | 2 hr at 750° C., 4 hr at 875° C. |
| Appearance | Glassy, translucent | Glassy, translucent |
| Ceramming cycle | 2 hr at 750° C., 4 hr at 900° C. | 2 hr at 750° C., 4 hr at 900° C. |
| Appearance | Glassy, translucent | Glassy, translucent |

In some embodiments, the glass precursor and/or the glass ceramic can be strengthened to include compressive stress (CS) that extends from a surface thereof to a depth of compression (DOC). The compressive stress regions are balanced by a central portion exhibiting a tensile stress. At the DOC, the stress crosses from a positive (compressive) stress to a negative (tensile) stress. In one or more embodiments, the glass article may be chemically strengthening by ion exchange or other methods known in the art. In some embodiments, the residual glass phase or the glass precursor to the glass ceramic comprises at least one of lithium sodium or potassium, which enables ion exchange. Ion exchange is commonly used to chemically strengthen glasses. In one particular example, alkali cations within a source of such cations (e.g., a molten salt, or "ion exchange," bath) are exchanged with smaller alkali cations within the glass to achieve a layer under a compressive stress (CS) extending from the surface of the glass to a depth of compression (DOC) within the glass phase. For example, potassium ions from the cation source are often exchanged with sodium and/or lithium ions within the glass phase, and the K+ concentration profile correlates with the compressive stress and depth of layer.

The glass ceramic or precursor glass may be ion exchanged by immersion in at least one ion exchange bath containing molten salts (e.g., nitrates, sulfides, halides, or the like) of at least one alkali metal such as lithium, sodium, or potassium. The ion exchange bath may contain a salt (or salts) of a single alkali metal (e.g., sulfides, nitrates, or halides of Li, Na, or K) or salts of two or more alkali metals (e.g., sulfides, nitrates, or halides of Li and Na, or sulfides, nitrates, or halides of Na and K). Ion exchange is carried out in the ion exchange bath at temperatures ranging from about 390° C. to about 550° C. for times ranging from about 0.5 hour to about 24 hours.

The precursor glass or glass ceramic, in some embodiments, is ion exchanged and has a compressive layer extending from a surface to a depth of compression (DOC) of at least about 10 μm or, in some embodiments, at least about 30 μm into the glass ceramic, or in some embodiments up to about 10, 15, 20 or 25% into the glass as measured by thickness (surface to center). In some embodiments, the compressive layer extends from the surface of the precursor glass or glass ceramic to a depth of up to about 20% of the thickness of the glass ceramic. In some embodiments, the precursor glass or glass ceramic may be strengthened to exhibit a surface compressive stress in a range from 250 MPa to 800 MPa or greater.

In the strengthened glass ceramic, the depth of the compressive layer may be determined by electron microprobe, glow-discharge optical emission spectroscopy (GDOES, which is a technique for measuring depth profiles of constituent elements in a solid sample by detecting emissions from atoms accommodated in plasma by sputtering), or similar techniques that can provide composition data as a function of depth, where data would show incorporation of Na (where $Na^+$ replaces $Li^+$ in the glass phase) and/or K at the surfaces. The DOC of a precursor glass may be measured by surface stress meter (FSM) using commercially available instruments such as the FSM-6000, manufactured by Orihara Industrial Co., Ltd. (Japan). Surface stress measurements rely upon the accurate measurement of the stress optical coefficient (SOC), which is related to the birefringence of the glass. SOC in turn is measured by those methods that are known in the art, such as fiber and four point bend methods, both of which are described in ASTM standard C770-98 (2013), entitled "Standard Test Method for Measurement of Glass Stress-Optical Coefficient," the contents of which are incorporated herein by reference in their entirety, and a bulk cylinder method. CS may also be measured by measured by FSM. As used herein CS may be the "maximum compressive stress" which is the highest compressive stress value measured within the compressive stress layer. In some embodiments, the maximum compressive stress is located at the surface of the precursor glass or glass ceramic. In other embodiments, the maximum compressive stress may occur at a depth below the surface, giving the compressive profile the appearance of a "buried peak."

The strengthened articles disclosed herein may be incorporated into another article such as an article with a display (or display articles) (e.g., consumer electronics, including mobile phones, tablets, computers, navigation systems, and the like), architectural articles, transportation articles (e.g., automotive, trains, aircraft, sea craft, etc.), appliance articles, or any article that would benefit from some transparency, scratch-resistance, abrasion resistance or a combination thereof. In other embodiments, the glass ceramic forms a portion of a consumer electronic product, such as a cellular phone or smart phone, laptop computer, tablet, or the like. Such consumer electronic products typically comprise a housing having front, back, and side surfaces, and include electrical components such as a power source, a controller, a memory, a display, and the like, which are at least partially internal to the housing. In some embodiments, the glass ceramic described herein comprises at least a portion of a protective element, such as, but not limited to, the housing and/or display of a consumer electronic product.

An exemplary article incorporating any of the strengthened articles disclosed herein is shown in FIGS. 5A and 5B. Specifically, FIGS. 5A and 5B show a consumer electronic device 500 including a housing 502 having front 504, back 506, and side surfaces 508; electrical components (not shown) that are at least partially inside or entirely within the housing and including at least a controller, a memory, and a display 510 at or adjacent to the front surface of the housing; and a cover substrate 512 at or over the front surface of the housing such that it is over the display. In some embodiments, at least one of the cover substrate 512 or a portion of housing 502 may include any of the strengthened articles disclosed herein.

The $ZrO_2$-toughened glass-ceramic materials described herein can have fracture toughness values, as measured by Chevron notch short bar methods (known in the art and described in ASTM procedure E1304-97), of at least 1 $MPa \cdot m^{1/2}$, 1.5 $MPa \cdot m^{1/2}$, 2 $MPa \cdot m^{1/2}$, 3 $MPa \cdot m^{1/2}$, or in some embodiments, at least 4 $MPa \cdot m^{1/2}$. In some embodiments, the fracture toughness is in a range from 1 $MPa \cdot m^{1/2}$, 1.5 $MPa \cdot m^{1/2}$, 2 $MPa \cdot m^{1/2}$, 3 $MPa \cdot m^{1/2}$, or 4 $MPa \cdot m^{1/2}$ to 6 $MPa \cdot m^{1/2}$, 8 $MPa \cdot m^{1/2}$, or 10 $MPa \cdot m^{1/2}$ and, in other embodiments, from about 1.5 $MPa \cdot m^{1/2}$, 2 $MPa \cdot m^{1/2}$, 3 $MPa \cdot m^{1/2}$ to 8 $MPa \cdot m^{1/2}$. Results of fracture toughness and flex strength measurements for selected samples are provided in Table 3. Examples 5-12 in Table 3 illustrate the increase in fracture toughness with increasing amounts of $ZrO_2$.

In some embodiments, the $ZrO_2$-toughened glass ceramic described herein is used in dental composites, restorative materials, and articles such as, but not limited to, fillings, bridges, splints, crowns, partial crowns, dentures, teeth, jackets, inlays, onlays, facings, veneers, facets, implants, cylinders, abutments and connectors. In addition to the glass ceramic, such dental composites, restorative materials, and articles may also include further additives such as, but not limited to, stabilizers, flavorings, colorants (e.g., Mn, V, Ti, Fe, Er, Co, Pr, Tb, Cr, Nd, Ce, V, Eu, Ho, Ni, and Cu, oxides and sulfides thereof, and combinations thereof), microbiocidal active ingredients, fluoride ion-releasing additives, optical brighteners, plasticizers, UV absorbers, and/or solvents such as water, ethanol, or corresponding solvent mixtures. The glass ceramic may be processed into the dental article using various methods including, but not limited to, injection molding, gel-casting, slip casting, or electroforming, hand forming, CAD/CAM methods, 3d printing, and other various rapid prototyping methods that are known in the art. The glass ceramic may, in some embodiments, be ground to powder, which may be then formed into a suspension, pellet, feedstock material or a pre-sintered blank prior being formed into the dental article.

Processes for Making Glass Ceramics and Glass Ceramic Precursors

Precursor glasses having the oxide contents listed in Table 1 can be made via traditional methods. For example, in some embodiments, the precursor glasses can be formed by thoroughly mixing the requisite batch materials (for example, using a turbular mixer) in order to secure a homogeneous melt, and subsequently placing into silica and/or platinum crucibles. The crucibles can be placed into a furnace and the glass batch melted and maintained at temperatures ranging from 1250-1650° C. for times ranging from about 6-16 hours. The melts can thereafter be poured into steel molds to yield glass slabs. Subsequently, those slabs can be transferred immediately to an annealer operating at about 500-650° C., where the glass is held at temperature for about 1 hour and subsequently cooled overnight. In another non-limiting example, precursor glasses are prepared by dry blending the appropriate oxides, carbonates, and mineral sources for a time sufficient to thoroughly mix the ingredients. The glasses are melted in platinum crucibles at temperatures ranging from about 1100° C. to about 1650° C. and held at temperature for about 16 hours. The resulting glass melts are then poured onto a steel table to cool. The precursor glasses are then annealed at appropriate temperatures.

Once the glass compositions have been made, the resulting precursor glasses can be cerammed by heat treating. Heat treating is carried out under conditions that lead to crystallization of the glass composition to make a ceramic. Generally, this is done via a two-phase heating process, wherein the glass is first heated to a lower temperature to induce nucleation, and then heated to a higher temperature to induce crystallization. Non-limiting conditions include first heating to 600° C. to 850° C., 635° C. to 800° C., or 650° C. to 750° C. for from 0.1 to 10 hours, 0.25 to 8 hours, 0.25 to 5 hours, 0.25 to 3 hours, 0.25 to 2 hours, 0.5 to 8 hours, 0.5 to 5 hours, 0.5 to 3 hours, 0.5 to 2 hours, 1 to 9 hours, 1 to 8 hours, 1 to 5 hours, 1 to 3 hours, or 1 to 2 hours, (called a nucleation step), followed by heating at 725° C. to 1000° C., 725° C. to 950° C., 725° C. to 900° C., or 750° C. to 850° C. for 0.1 to 8 hours 0.1 to 10 hours, 0.25 to 8 hours, 0.25 to 5 hours, 0.25 to 3 hours, 0.25 to 2 hours, 0.5 to 8 hours, 0.5 to 5 hours, 0.5 to 3 hours, 0.5 to 2 hours, 1 to 9 hours, 1 to 8 hours, 1 to 5 hours, 1 to 3 hours, 1 to 2 hours, 2 to 9 hours, 2 to 8 hours, 2 to 5 hours, 2 to 3 hours, or 2 to 4 hours (a crystal growth step).

In an example embodiment, a precursor glass comprising at least about 18 wt % $Li_2O$, up to about 5 wt % $Al_2O_3$, and at least about 4 wt % $ZrO_2$ is first provided. The precursor glass is next heat-treated or "cerammed" to form the glass ceramic. The ceramming step comprises first heating the precursor material at a first temperature in a range from about 600° C. to about 750° C. for a first time period ranging from about 15 minutes to about 2.5 hours or, in some embodiments, from about 15 minutes to about one hour or, in other embodiments, from about 1.5 hours to about 2.5 hours. Following the first heating step, the material is heated at a second temperature in a range from about 725° C. to about 1000° C. for a second time period ranging from about 0.5 hour to about 5 hours, or, in some embodiments, from about 0.5 hour to about 5 hours or, in other embodiments, from about 3 hours to about 5 hours to form the glass ceramic.

Alternatively, in some embodiments, the precursor material may comprise a precursor glass and a ceramic powder, wherein the ceramic powder comprises $ZrO_2$. In this embodiment, the precursor glass may be ground to a powder having an average grain size of less than about 10 μm and then mixed with the ceramic powder. The glass ceramic may then, in some embodiments, be sintered at temperatures ranging from about 650° C. to about 800° C. for a time ranging from about 0.5 hour up to about 4 hours. In other embodiments, the glass ceramic may be hot pressed to form a near-net shape.

While in some embodiments $ZrO_2$-toughened glass-ceramics have been made by adding $ZrO_2$ particles to a powdered glass-ceramic precursor glass, with subsequent sintering, such methods involve mixing of two dissimilar powders, which can lead inhomogeneity in the final $ZrO_2$-glass-ceramic product. In addition, the sintering times and temperatures that are used may promote more grain growth than desired or may have other detrimental effects on microstructure. In the sintering method, nucleation and growth of the desired phases may be a mixture of surface and bulk nucleation, thereby resulting in microstructures that are difficult to control or repeat. All of these challenges could result in compromised strength and/or fracture toughness values of the final material. Furthermore, sintering is often done at elevated pressures in an attempt to reach full density of the final product. Achieving full density may or may not be achieved and porosity may be an issue for realizing high strength and fracture toughness materials.

Producing $ZrO_2$-containing glass ceramics from homogeneous glass precursors, as described herein, addresses many of the above issues. The glasses may be homogeneously nucleated and the nucleation and growth steps can be further controlled to yield final products with optimized microstructures and phase assemblages. Full density is achieved through the ceramming of the dense precursor glass without the use of elevated pressure. Precursor glasses are produced by conventional glass melting and forming techniques. Whereas some glass compositions containing high amounts of $ZrO_2$ must be melted at high temperature, many of the $Li_2O$ and MgO-containing compositions described herein are easily melted at low temperatures (e.g., <1650° C.). Further, additional phases, previously described hereinabove such as lithium metasilicate, lithium disilicate, b-quartz solid solution, b-spodumene solid solution, may also be precipitated in the glass ceramic. In some embodiments, these microstructures and phase assemblages are not easily obtainable using ceramic processing routes.

Another advantage of the materials described herein is that they have the ability to be partially cerammed to the lithium metasilicate phase, then machined and/or finished, and then cerammed into the full high fracture toughness final glass ceramic. When ceramming, lithium metasilicate comes out first (leaving a $ZrO_2$-rich glass phase), allowing for shaping or machining, then further ceramming to get t-$ZrO_2$/LDS phases. In some embodiments, the $ZrO_2$-toughened glass ceramic described herein is used in applications such as, but not limited to valves, blades, cutting tools, knives, components for semiconductor manufacturing (cover rings, etch nozzles, RF shields, etc.), oil and gas drilling components (downhole pump plungers, control valves, etc.), and ferrules for optical fiber connectors, where high resistance to mechanical wear is desired.

The glass ceramics and precursor glasses described herein are easily cast or rolled as homogeneous glasses, and final geometries such as sheets or boules are obtainable. The resultant glass ceramic can be provided as a sheet, which can then be reformed by pressing, blowing, bending, sagging, vacuum forming, or other means into curved or bent pieces of uniform thickness. Reforming can be done before thermally treating or the forming step can also serve as a thermal treatment step where both forming and thermally treating are performed substantially simultaneously.

EXAMPLES

FIGS. 1A and 1B are scanning electron microscopy (SEM) images showing embodied glass ceramics having $ZrO_2$ and other phases present in samples. FIG. 1A is an image of a glass ceramic material (composition Example 6 in Table 3) that is cerammed by first heating at 750° C. for 2 hours and then heating at 900° C. for 4 hours, and FIG. 1B is an image of a glass ceramic material (composition Example 10 in Table 3) that is cerammed by first heating at 800° C. for 2 hours and then heating at 900° C. for 4 hours. The microstructure of the materials in both images is homogeneous. The dark gray rods 120 in FIGS. 1A and 1B are lithium disilicate and the white phases 110 in FIGS. 1A and 1B are $ZrO_2$. The $ZrO_2$ grains 110 are on the order of about 1 μm in size. X-Ray diffraction studies of these samples reveals that the zirconia phase is primarily tetragonal $ZrO_2$. The sample that is cerammed at 900° C. (FIG. 1B) appears by SEM to contain a higher amount of the tetragonal $ZrO_2$ phase than the sample cerammed at 800° C. for 4 hours (FIG. 1A).

Figure 2B:
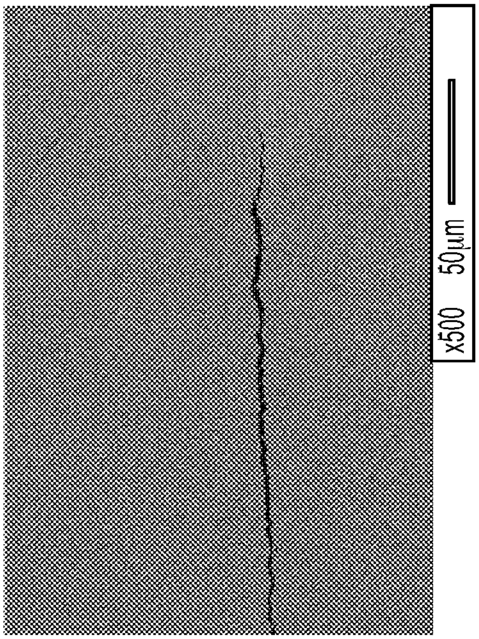
FIGS. 2A-D are SEM images showing the indents after a Vickers indentation at 50 kgf of Example 8. The example composition was cerammed at 750° C. for 2 hours, then 875° C. for 4 hours. The tortuous crack path and crack deflection by the lithium disilicate and tetragonal zirconia are visible in example.
Figure 2A:
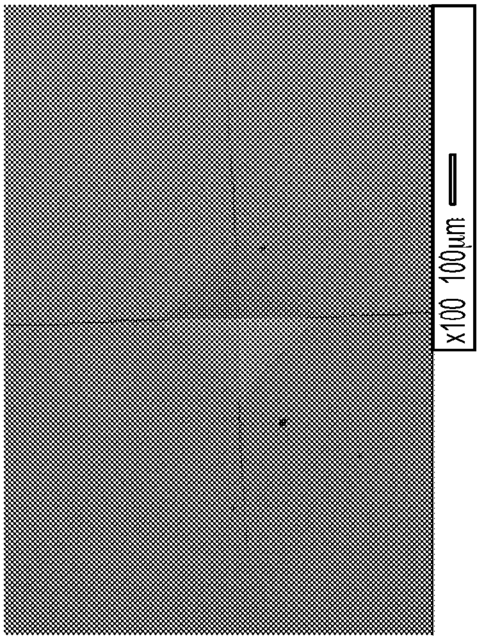
Figure 2C:
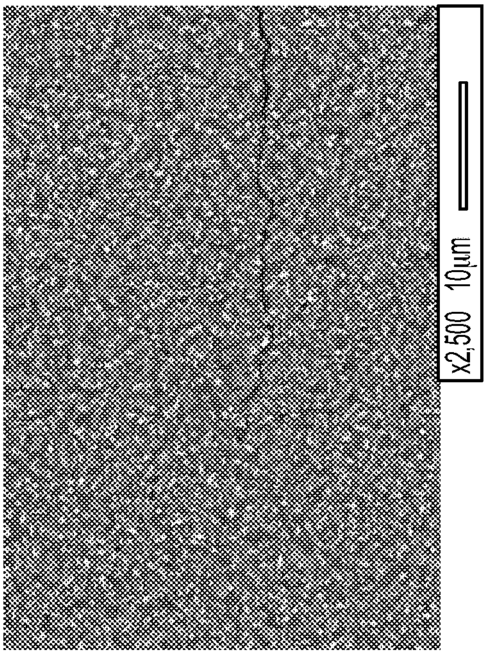
Figure 2D:
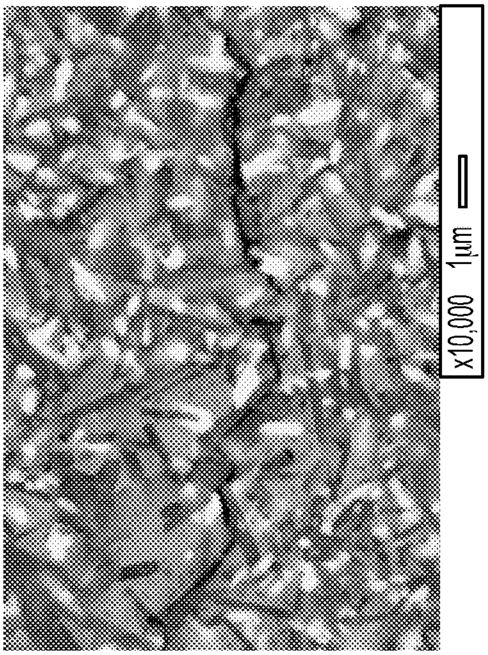

FIGS. 2A-D are SEM images of an indented area on the surface of a glass ceramic (composition Example 6 in Table 3) that is cerammed by first heating at 750° C. for 2 hours and then heating at 875° C. for 4 hours, showing a crack at different magnifications (FIG. 2A at 100× magnification; FIG. 2B at 500×; FIG. 2C at 2500×; FIG. 2D at 10,000×). Under indentation load of 50 kgf, the sample exhibits crack deflection and tortuous crack path which are indicative of toughening mechanisms.

Figure 3A:
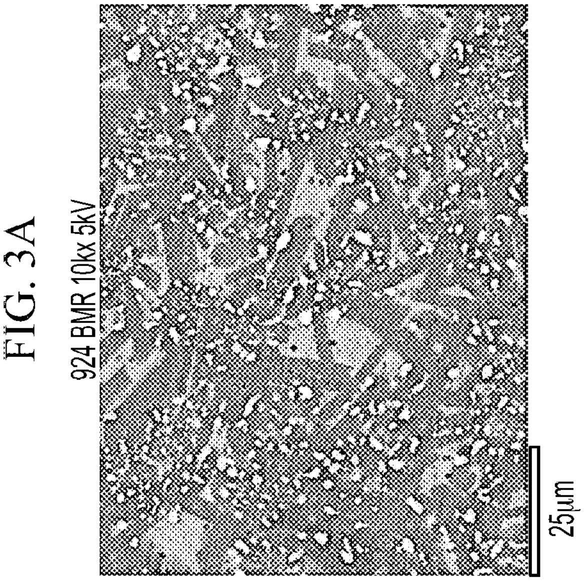
FIGS. 3A-3D are an SEM image of embodiment Example 8 (FIG. 3A), along with SEM elemental mapping of some of the constituents of Example 8, where
Figure 3B:
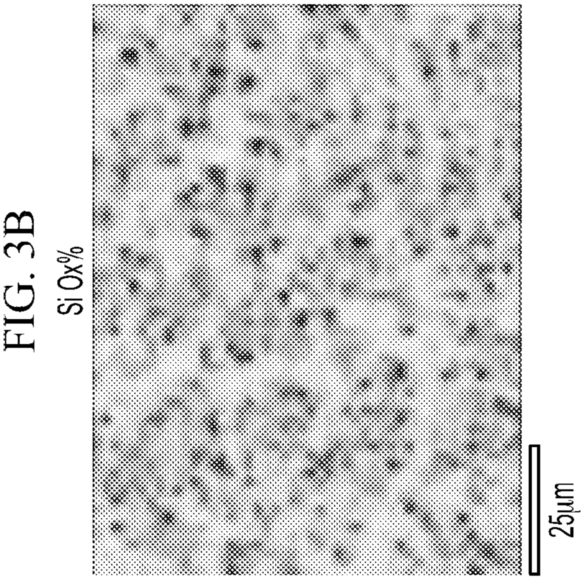
Figure 3D:
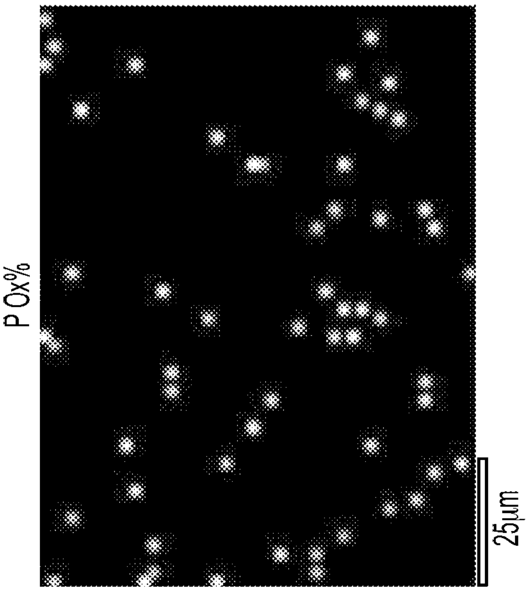
Figure 3C:
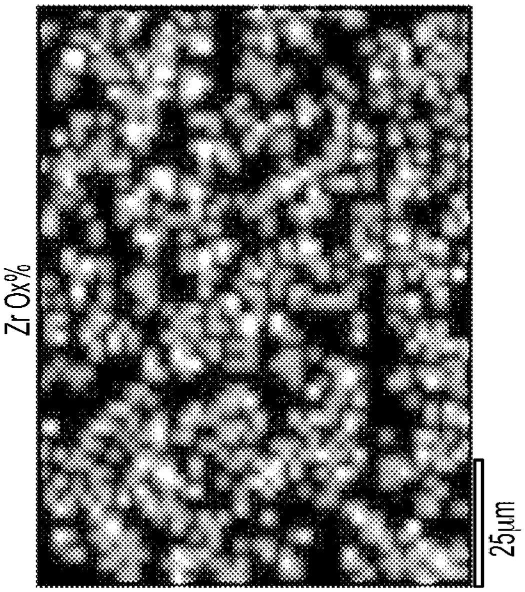
Figure 4A:
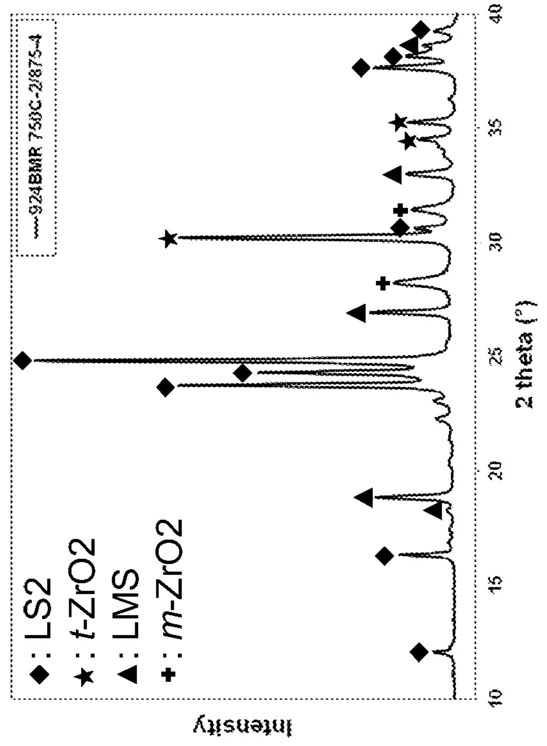
FIGS. 4A-4D are X-ray diffraction spectra showing phase assemblages of embodied glass-ceramics. The figures show that lithium disilicate (LS2) and tetragonal $ZrO_2$ (t-$ZrO_2$) are present in the various embodiments along with a number of other phases (lithium metasilicate (LMS), monoclinic $ZrO_2$ (m-$ZrO_2$)).
Figure 4B:
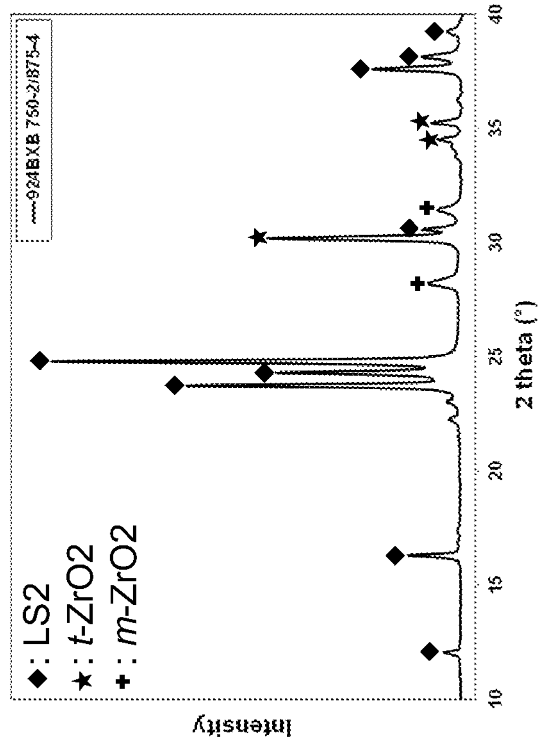
Figure 4D:
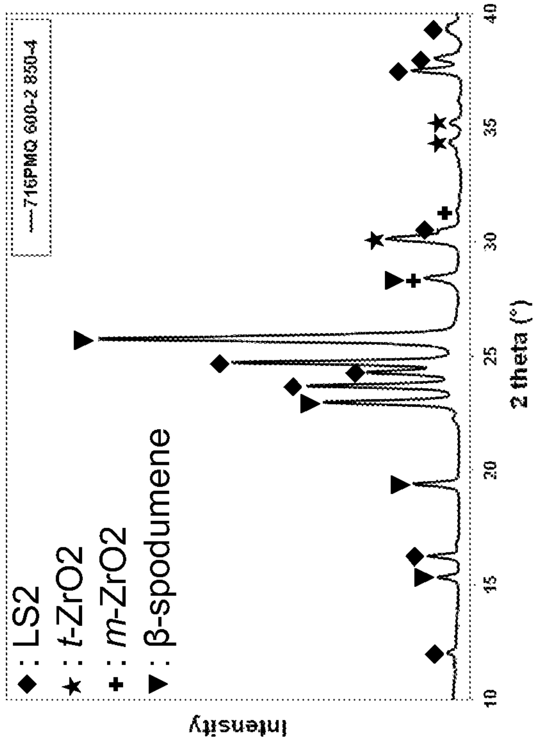
Figure 4C:
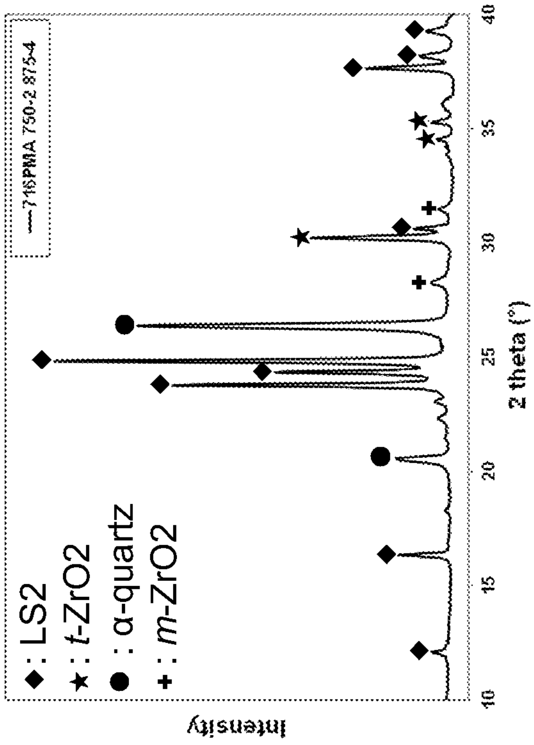

FIGS. 3A-D show the crystal microstructure of an embodiment (Example 8) along with SEM elemental mapping of some of the constituents of Example 8, where FIG. 3B shows the silicon present in the material, FIG. 3C shows the zirconia, and FIG. 3D shows the phosphorous FIGS. 4A-4D are X-ray diffraction spectra showing phase assemblages of embodied glass-ceramics. The figures show that lithium disilicate (LS2) and tetragonal $ZrO_2$ (t-$ZrO_2$) are present in the various embodiments along with a number of other phases (lithium metasilicate (LMS), monoclinic $ZrO_2$ (m-$ZrO_2$)). FIG. 4A shows the phase assemblage for Example 8, FIG. 4B for Example 14, FIG. 4C for Example 40, and FIG. 4D for Example 44. All examples were cerammed at 750° C. for 2 hours, then 875° C. for 4 hours, except Example 44 which was cerammed at 750° C. for 2 hours, then 850° C. for 4 hours.

Figure 5:
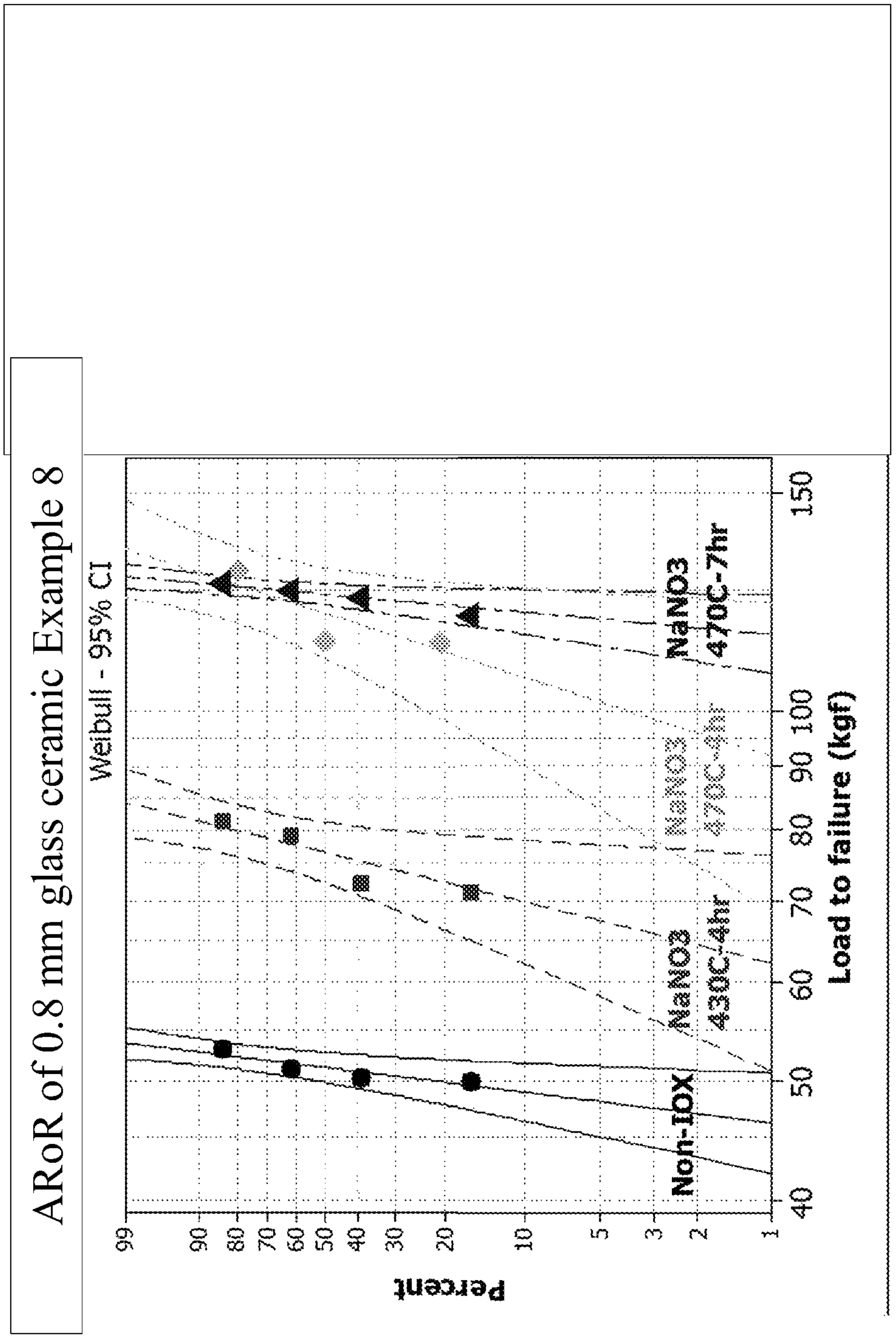
FIG. 5 is a plot of abraded ring-on-ring (ARoR) data obtained for 0.8 mm-thick samples of a non-ion exchanged and ion-exchanged $ZrO_2$-toughened glass ceramic (Example 8), which ion exchanged for a number of different times and temperatures.

FIG. 5 is a plot of abraded ring-on-ring (ARoR) data obtained for 0.8 mm-thick samples of a non-ion exchanged and ion-exchanged $ZrO_2$-toughened glass ceramic (Example 8), which ion exchanged for a number of different times and temperatures. The glass ceramic was cerammed by first heating at 700° C. for 2 hours and then heating at 850° C. for 4 hours. The ring-on-ring test is a flexural strength measurement known in the art for testing flat glass and glass ceramic specimens and is described in ASTM C1499-09 (2013), entitled "Standard Test Method for Monotonic Equibiaxial Flexural Strength of Advanced Ceramics at Ambient Temperature." ASTM C1499-09 (2013) serves as the basis for the ring-on-ring test methodology described herein. In some instances, the glass ceramic samples are abraded prior to ring-on-ring testing with 15 grit silicon carbide (SiC) particles that are delivered to the glass sample using the method and apparatus described in Annex A2, entitled "Abrasion Procedures," of ASTM C158-02 (2012), entitled "Standard Test Methods for Strength of Glass by Flexure (Determination of Modulus of Rupture). The contents of ASTM C1499-09 (2013) and ASTM C158-02 (2012), Annex 2, are incorporated herein by reference in their entirety. The table shows that the glass ceramics embodied herein are capable of undergoing ion exchange and that such ion-exchanged glass ceramics have improved load to failure values that correlate with time and temperature in the ion exchange bath.

Figure 6A:
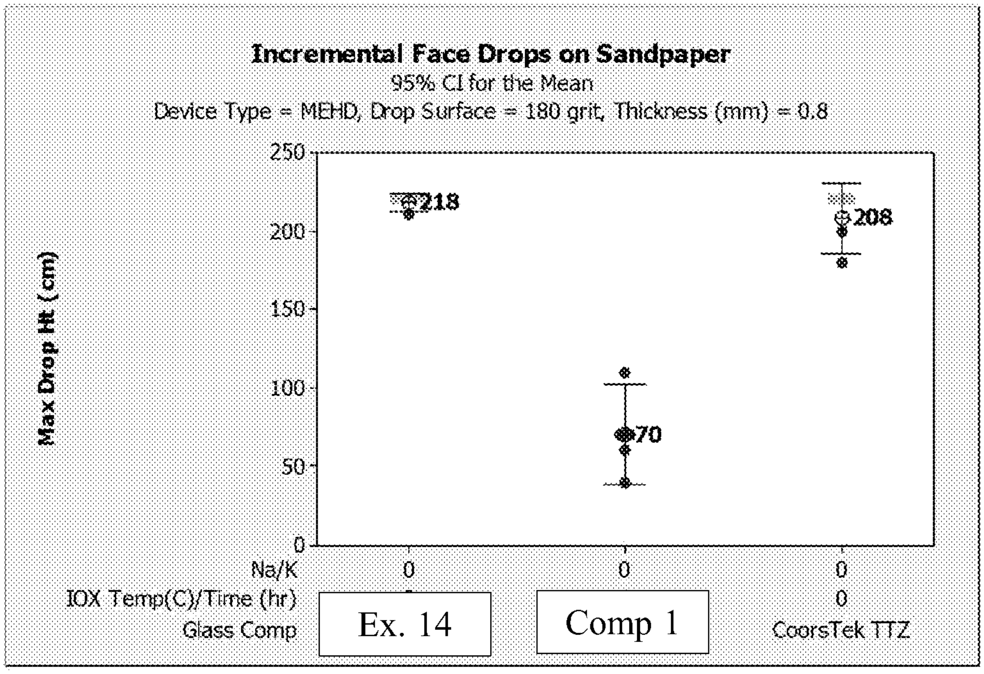
FIGS. 6A and 6B are comparisons of drop performance for example embodiments (Example 14) and $ZrO_2$ ceramics. All parts are 0.8 mm thick, dropped on 180 grit sandpaper and then survivors on 30 grit sand paper. Example 14 was cerammed at 750° C. for 2 hours, then 875° C. for 4 hours; Comp 1 is a reference transparent glass-ceramic; CoorsTek TTZ is a MgO-stabilized $ZrO_2$ ceramic.
Figure 6B:
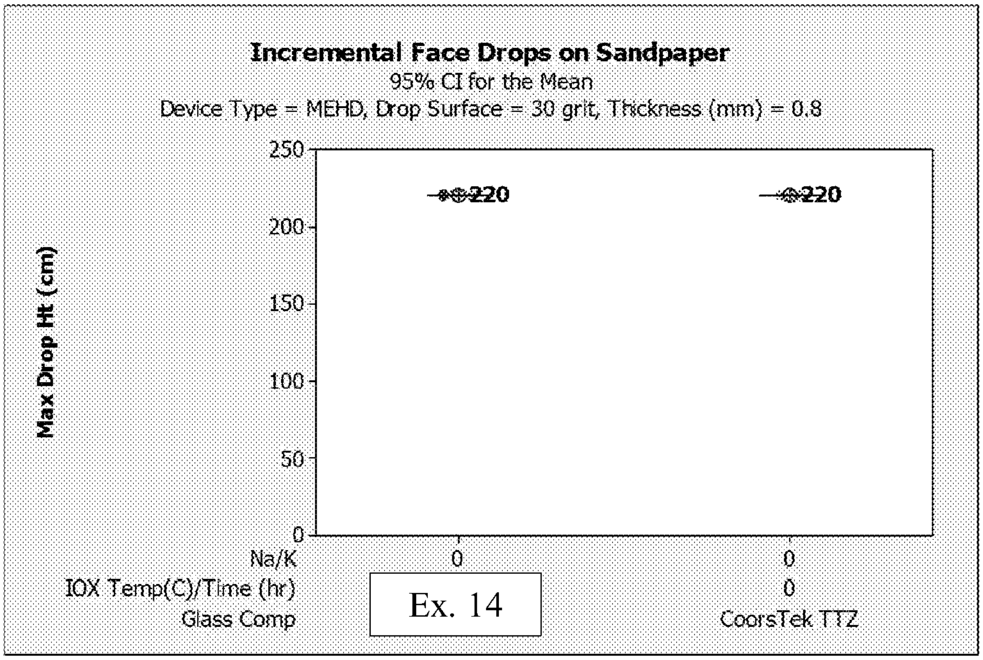
Figure 9A:
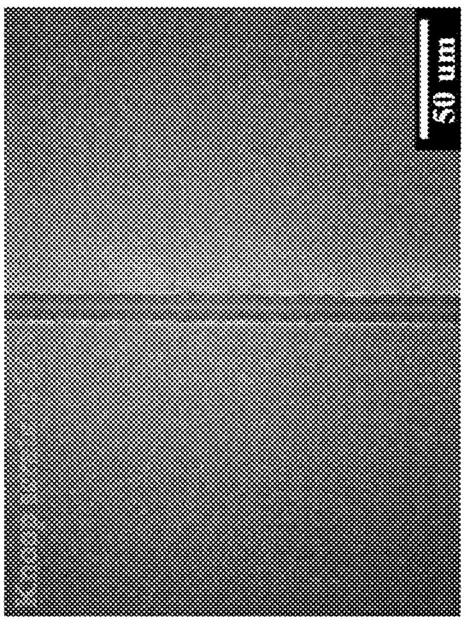
FIGS. 9A-9C are micrographs of scratch tests done using a Knoop tip at 14 N and 16 N loads for Example 8. The example composition was cerammed at 750° C. for 2 hours, then 875° C. for 4 hours.
Figure 9B:
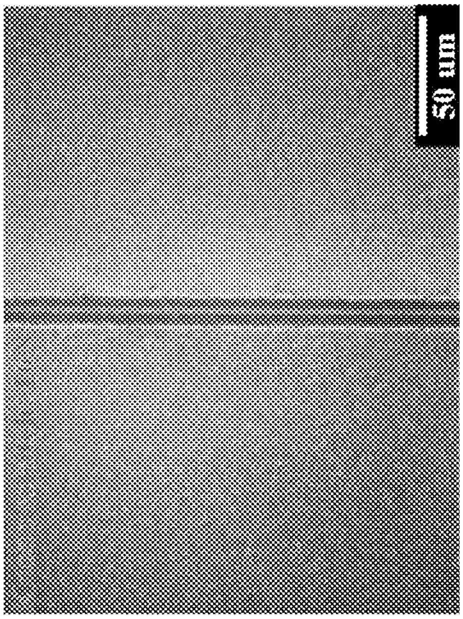
Figure 9C:
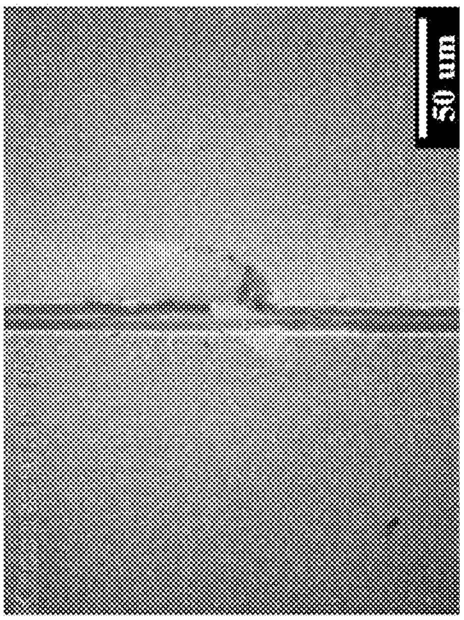

FIGS. 6A and 6B are comparisons of drop performance for example embodiments (Example 14) and $ZrO_2$ ceramics. All parts are 0.8 mm thick, dropped on 180 grit sandpaper and then survivors on 30 grit sandpaper. Example 14 was cerammed at 750° C. for 2 hours, then 875° C. for 4 hours; Comp 1 is a reference transparent glass-ceramic; CoorsTek TTZ is a MgO-stabilized $ZrO_2$ ceramic. The embodied compositions have favorable properties when compared to the transparent glass ceramic and in line with the CoorsTek material. Similarly, FIGS. 9A-9C are micrographs of scratch tests done using a Knoop tip at 14 N and 16 N loads for Example 8. The example composition was cerammed at 750° C. for 2 hours, then 875° C. for 4 hours.

Figure 7:
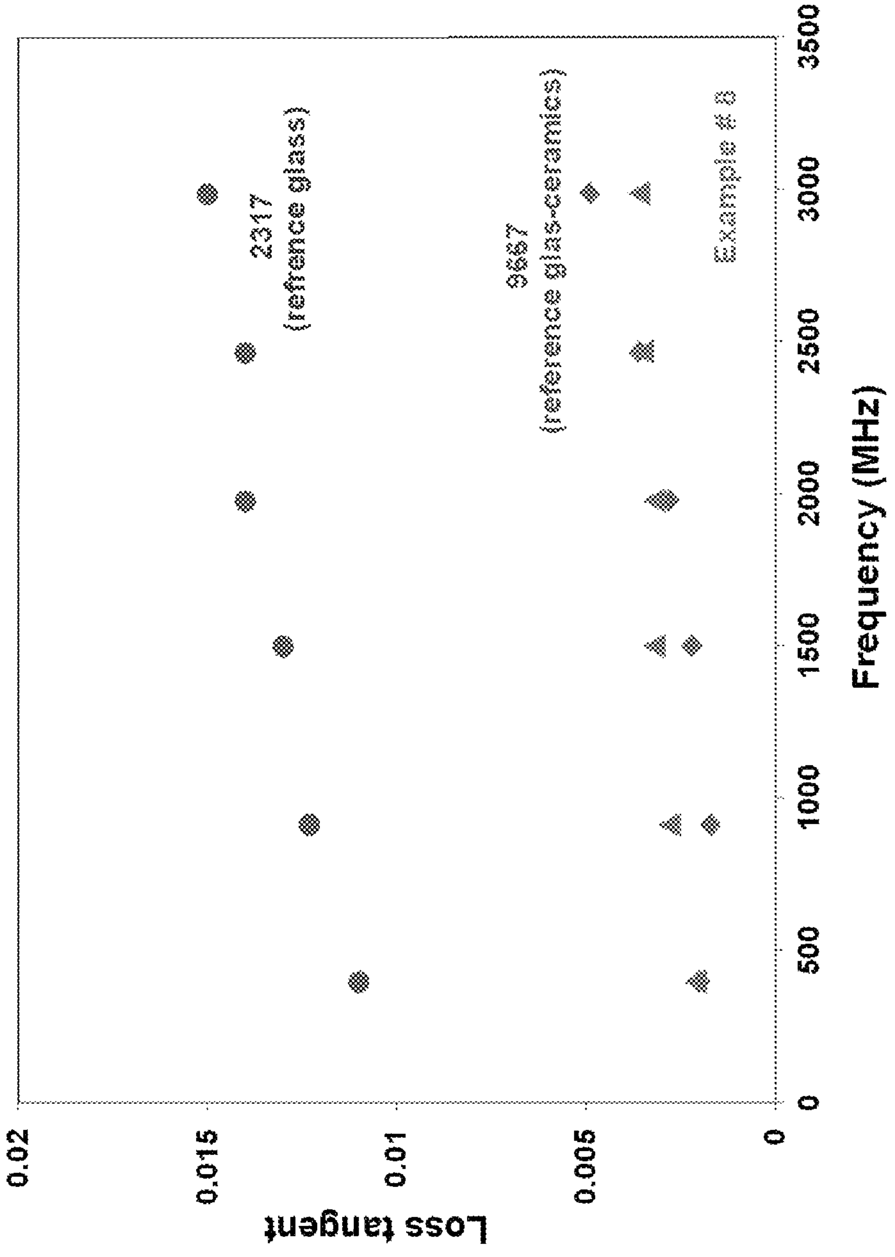
FIG. 7 shows the loss tangent of Example 8 versus a reference glass and reference glass ceramic. The example composition was cerammed at 750° C. for 2 hours, then 875° C. for 4 hours.
Figure 8:
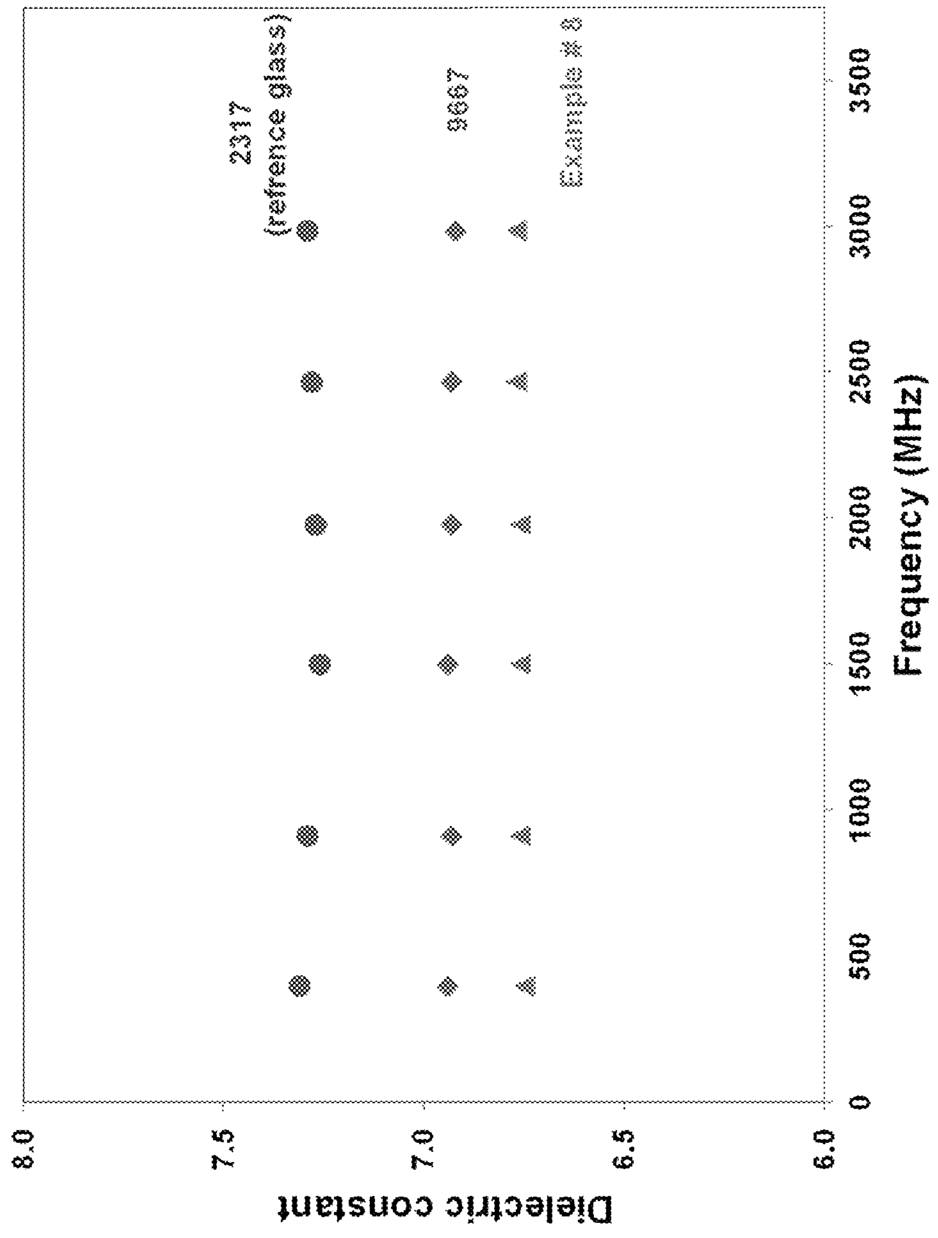
FIG. 8 shows the dielectric constant of Example 8 versus a reference glass and reference glass ceramic. The example composition was cerammed at 750° C. for 2 hours, then 875° C. for 4 hours.

The color of Example 8 is measured in CIELAB color space coordinates (determined from reflectance spectra measurements using a spectrophotometer, with illuminant D65 and specular reflectance excluded), a*: −0.15, b*: −0.31, and L*: 98.8. FIG. 7 shows the loss tangent of Example 8 versus a reference glass and reference glass ceramic. The example composition was cerammed at 750° C. for 2 hours, then 875° C. for 4 hours. FIG. 8 shows the dielectric constant of Example 8 versus a reference glass and reference glass ceramic. The example composition was cerammed at 750° C. for 2 hours, then 875° C. for 4 hours.

While typical embodiments have been set forth for the purpose of illustration, the foregoing description should not be deemed to be a limitation on the scope of the disclosure or appended claims. Accordingly, various modifications, adaptations, and alternatives may occur to one skilled in the art without departing from the spirit and scope of the present disclosure or appended claims.

The invention claimed is:

1. A glass-ceramic, comprising:
- a crystalline phase comprising:
  - crystals of tetragonal zirconia, and
  - crystals of lithium disilicate; and
- a glass phase; and
- wherein the crystals of tetragonal zirconia and lithium disilicate comprise 60-95 wt % of the total glass-ceramic; and
- wherein the tetragonal zirconia comprises a weight percent (wt %) of total zirconia in the glass-ceramic, measured as the (((weight of the tetragonal zirconia)/(total weight of zirconia in the glass-ceramic))*100), and wherein the tetragonal zirconia comprises 40-95 wt % of the total zirconia in the glass-ceramic.

2. The glass-ceramic of claim 1, wherein the lithium disilicate comprises a weight percent (wt %) of the total glass-ceramic, measured as the (((weight of the lithium disilicate)/(total weight the glass-ceramic))*100), and wherein the lithium disilicate comprises from 25-60 wt % of the total glass-ceramic.

3. The glass-ceramic of claim 1, wherein the crystalline phase further comprises crystals selected from the group consisting of lithium aluminosilicate, cristobalite, β-spodumene, lithiophosphate, lithium orthophosphate, β-quartz solid solution, baddeleyite, lithium metasilicate, monoclinic zirconia, cubic zirconia, zekzerite, $(Na,Li)ZrSi_6O_{18}$, and combinations thereof.

4. The glass-ceramic of claim 1, wherein the crystalline phase further comprises crystals of monoclinic zirconia and crystals selected from the group consisting of lithium aluminosilicate, β-spodumene solid solution, β-quartz solid solution, or α-quartz.

5. The glass-ceramic of claim 1, wherein the glass-ceramic comprises >0-14 mol % of a sum of alkali metal oxides $Na_2O$, $K_2O$, and $Cs_2O$.

6. The glass-ceramic of claim 1, wherein the glass-ceramic comprises >0-10 mol % of a sum of alkaline earth metal oxides MgO, CaO, SrO, and BaO.

7. The glass-ceramic of claim 1, wherein the glass-ceramic comprises >0-5 mol % of a sum of oxides $Sc_2O_3$, $Y_2O_3$, $La_2O_3$, $Ce_2O_3$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, and $Lu_2O_3$.

8. A glass-ceramic, comprising:
- a composition in terms of representative oxides comprising:
  - 58-69 mol % $SiO_2$,
  - 25-36 mol % $Li_2O$,
  - 6-15 mol % $ZrO_2$,
  - >0-5 mol % $Al_2O_3$;
  - 0-5 mol % $Na_2O$;
  - 0-5 mol % $B_2O_3$; and
  - 0.2-3 mol % $P_2O_5$; and
- crystalline and glass phases, the crystalline phase comprising:
  - crystals of tetragonal zirconia; and
  - crystals of lithium disilicate.

9. The glass-ceramic of claim 8, further comprising >0-4 mol % of a color component comprising $Fe_2O_3$, $V_2O_5$, $Cr_2O_3$, $TiO_2$, $MnO_2$, NiO, ZnO, CuO, NiO, and/or $Co_3O_4$.

10. The glass-ceramic of claim 8, wherein the glass-ceramic exhibits a color presented in CIELAB color space coordinate a* of from about −1 to about +3.

11. The glass-ceramic of claim 8, wherein the glass-ceramic exhibits a color presented in CIELAB color space coordinate b* of from about −7 to about +3.

12. The glass-ceramic of claim 8, wherein the glass-ceramic exhibits a color presented in CIELAB color space coordinate L* of greater than 85.

13. A glass-ceramic, comprising:
a crystalline phase comprising:
crystals of tetragonal zirconia, wherein an average crystal size along a longest dimension for the crystals of tetragonal zirconia is in a range from 100 nm to 10 μm; and
crystals of lithium disilicate; and
a glass phase; and
an ion-exchanged layer having a depth of compression of at least 10 μm.

14. The glass-ceramic of claim 13, further comprising a composition in terms of representative oxides comprising:
50-80 mol % $SiO_2$;
18-40 mol % $Li_2O$;
1.5-25 mol % $ZrO_2$; and
greater than 0-5 mol % $P_2O_5$.

15. The glass-ceramic of claim 13, wherein an average crystal size along a longest dimension for crystals of the lithium disilicate in a range from 2 μm to 20 μm.

16. The glass-ceramic of claim 13, the glass phase is 1 to 50 wt % of the glass-ceramic.

17. The glass-ceramic of claim 13, wherein the crystalline phase further comprises monoclinic zirconia.

18. A glass-ceramic, comprising:
a crystalline phase comprising:
crystals of tetragonal zirconia, and
crystals of lithium disilicate; and
a glass phase; and
wherein the crystals of tetragonal zirconia and lithium disilicate comprise 60-95 wt % of the total glass-ceramic; and
wherein the lithium disilicate comprises a weight percent (wt %) of the total glass-ceramic, measured as the (((weight of the lithium disilicate)/(total weight the glass-ceramic))*100), and wherein the lithium disilicate comprises from 25-60 wt % of the total glass-ceramic.

19. The glass-ceramic of claim 18, wherein the crystalline phase further comprises crystals selected from the group consisting of lithium aluminosilicate, cristobalite, β-spodumene, lithiophosphate, lithium orthophosphate, β-quartz solid solution, baddeleyite, lithium metasilicate, monoclinic zirconia, cubic zirconia, zekzerite, $(Na,Li)ZrSi_6O_{18}$, and combinations thereof.

20. The glass-ceramic of claim 18, wherein the crystalline phase further comprises crystals of monoclinic zirconia and crystals selected from the group consisting of lithium aluminosilicate, β-spodumene solid solution, β-quartz solid solution, or α-quartz.

21. The glass-ceramic of claim 18, wherein the glass-ceramic comprises >0-14 mol % of a sum of alkali metal oxides $Na_2O$, $K_2O$, and $Cs_2O$.

22. The glass-ceramic of claim 18, wherein the glass-ceramic comprises >0-10 mol % of a sum of alkaline earth metal oxides MgO, CaO, SrO, and BaO.

23. The glass-ceramic of claim 18, wherein the glass-ceramic comprises >0-5 mol % of a sum of oxides $Sc_2O_3$, $Y_2O_3$, $La_2O_3$, $Ce_2O_3$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, and $Lu_2O_3$.

24. A glass-ceramic, comprising:
a composition in terms of representative oxides comprising:
50-80 mol % $SiO_2$,
18-40 mol % $Li_2O$,
1.5-25 mol % $ZrO_2$, and
greater than 0-5 mol % $P_2O_5$; and
crystalline and glass phases, the crystalline phase comprising:
crystals of tetragonal zirconia; and
crystals of lithium disilicate;
wherein the glass-ceramic exhibits a color presented in CIELAB color space coordinate a* of from about −1 to about +3.

25. The glass-ceramic of claim 24, further comprising >0-4 mol % of a color component comprising $Fe_2O_3$, $V_2O_5$, $Cr_2O_3$, $TiO_2$, $MnO_2$, NiO, ZnO, CuO, NiO, and/or $Co_3O_4$.

26. The glass-ceramic of claim 24, wherein the glass-ceramic exhibits a color presented in CIELAB color space coordinate b* of from about −7 to about +3.

27. The glass-ceramic of claim 24, wherein the glass-ceramic exhibits a color presented in CIELAB color space coordinate L* of greater than 85.

28. A glass-ceramic, comprising:
a composition in terms of representative oxides comprising:
50-80 mol % $SiO_2$,
18-40 mol % $Li_2O$,
1.5-25 mol % $ZrO_2$, and
greater than 0-5 mol % $P_2O_5$; and
crystalline and glass phases, the crystalline phase comprising:
crystals of tetragonal zirconia; and
crystals of lithium disilicate;
wherein the glass-ceramic exhibits a color presented in CIELAB color space coordinate b* of from about −7 to about +3.

29. The glass-ceramic of claim 28, further comprising >0-4 mol % of a color component comprising $Fe_2O_3$, $V_2O_5$, $Cr_2O_3$, $TiO_2$, $MnO_2$, NiO, ZnO, CuO, NiO, and/or $Co_3O_4$.

30. The glass-ceramic of claim 28, wherein the glass-ceramic exhibits a color presented in CIELAB color space coordinate L* of greater than 85.

31. A glass-ceramic, comprising:
a composition in terms of representative oxides comprising:
50-80 mol % $SiO_2$,
18-40 mol % $Li_2O$,
1.5-25 mol % $ZrO_2$, and
greater than 0-5 mol % $P_2O_5$; and
crystalline and glass phases, the crystalline phase comprising:
crystals of tetragonal zirconia; and
crystals of lithium disilicate;
wherein the glass-ceramic exhibits a color presented in CIELAB color space coordinate L* of greater than 85.

32. The glass-ceramic of claim 31, further comprising >0-4 mol % of a color component comprising $Fe_2O_3$, $V_2O_5$, $Cr_2O_3$, $TiO_2$, $MnO_2$, NiO, ZnO, CuO, NiO, and/or $Co_3O_4$.

33. A glass-ceramic, comprising:
a crystalline phase comprising:
crystals of tetragonal zirconia, and
crystals of lithium disilicate, wherein an average crystal size along a longest dimension for the crystals of lithium disilicate is in a range from 2 μm to 20 μm;
a glass phase; and an ion-exchanged layer having a depth of compression of at least 10 μm.

34. The glass-ceramic of claim 33, further comprising a composition in terms of representative oxides comprising:

50-80 mol % $SiO_2$;

18-40 mol % $Li_2O$;

1.5-25 mol % $ZrO_2$; and greater than 0-5 mol % $P_2O_5$.

35. The glass-ceramic of claim 33, the glass phase is 1 to 50 wt % of the glass-ceramic.

36. The glass-ceramic of claim 33, wherein the crystalline phase further comprises monoclinic zirconia.

37. A glass-ceramic, comprising:

a crystalline phase comprising:

crystals of tetragonal zirconia, and crystals of lithium disilicate;

a glass phase, where the glass phase is 1 to 50 wt % of the glass-ceramic; and an ion-exchanged layer having a depth of compression of at least 10 μm.

38. The glass-ceramic of claim 37, further comprising a composition in terms of representative oxides comprising:

50-80 mol % $SiO_2$;

18-40 mol % $Li_2O$;

1.5-25 mol % $ZrO_2$; and greater than 0-5 mol % $P_2O_5$.

39. The glass-ceramic of claim 37, wherein the crystalline phase further comprises monoclinic zirconia.

* * * * *